United States Patent
Norman et al.

(10) Patent No.: US 6,603,041 B2
(45) Date of Patent: Aug. 5, 2003

(54) BICYCLIC ENAMIDE DERIVATIVES

(75) Inventors: Timothy John Norman, Great Missenden (GB); John Robert Porter, Chinnor (GB); John Clifford Head, Maidenhead (GB); Andrew James Ratcliffe, Brentford (GB)

(73) Assignee: Celltech R & D Limited (GB)

( * ) Notice: Subject to any disclaimer, the term of this patent is extended or adjusted under 35 U.S.C. 154(b) by 0 days.

(21) Appl. No.: 09/947,107

(22) Filed: Sep. 5, 2001

(65) Prior Publication Data

US 2002/0072607 A1 Jun. 13, 2002

(30) Foreign Application Priority Data

Sep. 6, 2000 (GB) ............................................. 0021898

(51) Int. Cl.[7] .......................... C07C 61/12; C07C 249/00
(52) U.S. Cl. ...................... 562/440; 562/498; 562/499; 562/440; 562/427; 562/433; 562/458
(58) Field of Search ................................ 562/400, 498, 562/499, 440, 427, 433, 458

(56) References Cited

U.S. PATENT DOCUMENTS 4,420,477 A * 12/1983 Tanaya et al.

FOREIGN PATENT DOCUMENTS

| WO | WO 99/37618 | 7/1999 |
| --- | --- | --- |
| WO | WO 99/61465 | 12/1999 |
| WO | WO 00/18759 | 4/2000 |
| WO | WO 00/20396 | 4/2000 |
| WO | WO 00/73260 | 12/2000 |
| WO | WO 01/79173 A2 | 10/2001 |
| WO | WO 01/79173 * | 10/2001 |

* cited by examiner

Primary Examiner—Paul J. Killos
Assistant Examiner—Hector M Reyes

(74) Attorney, Agent, or Firm—Woodcock Washburn LLP

(57) ABSTRACT

Enamide derivatives of formula (1) are described:

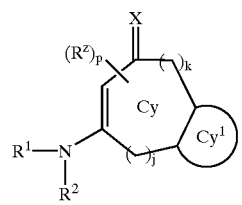

(1)

wherein $R^1$ is a group $Ar^1L^2Ar^2Alk$- in which $Ar^1$ is an optionally substituted aromatic or heteroaromatic group, $L^2$ is a covalent bond or a linker atom or group, $Ar^2$ is an optionally substituted arylene or heteroarylene group and Alk is a chain —$CH_2$—$CH(R)$—, —$CH$=$C(R)$— or

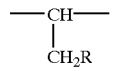

in which R is a carboxylic acid (—$CO_2H$) or a derivative or biostere thereof;

$R^2$ is a hydrogen atom or a $C_{1-6}$alkyl group;

X is an O or S atom or the group $NR^{30}$ group;

j and k is each zero or the integer 1 or 2 provided that the sum of j and k is zero or the integer 1 or 2;

$Cy^1$ is an optionally substituted cycloaliphatic, heterocycloaliphatic, aromatic or heteroaromatic group;

and the salts, solvates, hydrates and N-oxides thereof.

The compnods are able to inhibit the binding of integrins to their ligands and are of use in the prophylaxis and treatment of immune or inflammatory disorders, or disorders including the inappropriate growth or migration of cells.

23 Claims, No Drawings

BICYCLIC ENAMIDE DERIVATIVES

This invention relates to a series of phenylalanine derivatives, to compositions containing them, to processes for their preparation, and to their use in medicine.

Over the last few years it has become increasingly clear that the physical interaction of inflammatory leukocytes with each other and other cells of the body plays an important role in regulating immune and inflammatory responses [Springer, T. A., Nature, 346, 425, (1990); Springer, T. A., Cell, 76, 301, (1994)]. Specific cell surface molecules collectively referred to as cell adhesion molecules mediate many of these interactions.

The adhesion molecules have been sub-divided into different groups on the basis of their structure. One family of adhesion molecules which is believed to play a particularly important role in regulating immune and inflammatory responses is the integrin family. This family of cell surface glycoproteins has a typical non-covalently linked heterodimer structure. At least 16 different integrin alpha chains and 8 different integrin beta chains have been identified [Newman, P. et al, Molecular Medicine Today, 304, (1996)]. The members of the family are typically named according to their heterodimer composition although trivial nomenclature is widespread in the field. Thus the integrin$\alpha 4\beta 1$ consists of the integrin alpha 4 chain associated with the integrin beta 1 chain, but is also widely referred to as Very Late Antigen 4 or VLA-4. Not all of the potential pairings of integrin alpha and beta chains have yet been observed in nature and the integrin family has been subdivided into a number of subgroups based on the pairings that have been recognised to date [Sonnenberg, A., Current Topics in Microbiology and Immunology, 184, 7, (1993)].

The importance of integrin function in normal physiological responses is highlighted by two human deficiency diseases in which integrin function is defective. Thus in the disease termed Leukocyte Adhesion Deficiency (LAD) there is a defect in one of the families of integrins expressed on leukocytes [Marlin, S. D. et al, J. Exp. Med. 164, 855, (1986)]. Patients suffering from this disease have a reduced ability to recruit leukocytes to inflammatory sites and suffer recurrent infections, which in extreme cases may be fatal. In the case of patients suffering from the disease termed Glanzman's thrombasthenia (a defect in a member of the beta 3 integrin family) there is a defect in blood clotting (Hodivala-Dilke, K. M., J. Clin. Invest. 103, 229, (1999)].

The potential to modify integrin function in such a way as to beneficially modulate cell adhesion has been extensively investigated in animal models using specific antibodies and peptides that block various functions of these molecules [e.g. Issekutz, T. B., J. Immunol. 149, 3394, (1992); Li, Z. et al, Am. J. Physiol. 263, L723, (1992); Mitjans, F. et al, J. Cell Sci. 108, 2825, (1995); Brooks, P. C. et al, J. Clin. Invest. 96, 1815, (1995); Binns, R. M. et al, J. Immunol. 157, 4094, (1996); Hammes, H.-P. et al, Nature Medicine 2, 529, (1996); Srivata, S. et al, Cardiovascular Res.36, 408 (1997)]. A number of monoclonal antibodies which block integrin function are currently being investigated for their therapeutic potential in human disease, and one, ReoPro, a chimeric antibody against the platelet integrin $\alpha IIb\beta 3$ is in use as a potent anti-thrombotic agent for use in patients with cardiovascular complications following coronary angioplasty.

Integrins recognize both cell surface and extracellular matrix ligands, and ligand specificity is determined by the particular alpha-beta subunit combination of the molecule [Newman, P., ibid]. One particular integrin subgroup of interest involves the $\alpha 4$ chain which can pair with two different beta chains $\beta 1$ and $\beta 7$ [Sonnenberg, A., ibid]. The $\alpha 4\beta 1$ pairing occurs on many circulating leukocytes (for example lymphocytes, monocytes, eosinophils and basophils) although it is absent or only present at low levels on circulating neutrophils. $\alpha 4\beta 1$ binds to an adhesion molecule (Vascular Cell Adhesion Molecule-1 also known as VCAM-1) frequently up-regulated on endothelial cells at sites of inflammation [Osborne, L., Cell, 62, 3, (1990)]. The molecule has also been shown to bind to at least three sites in the matrix molecule fibronectin [Humphries, M. J. et al, Ciba Foundation Symposium, 189, 177, (1995)]. Based on data obtained with monoclonal antibodies in animal models it is believed that the interaction between $\alpha 4\beta 1$ and ligands on other cells and the extracellular matrix plays an important role in leukocyte migration and activation [Yednock, T. A. et al, Nature, 356, 63, (1992); Podolsky, D. K. et al, J. Clin. Invest. 92, 372, (1993); Abraham, W. M. et al, J. Clin. Invest. 93, 776, (1994)].

The integrin generated by the pairing of $\alpha 4$ and $\beta 7$ has been termed LPAM-1 [Holzmann, B. and Weissman, I. L., EMBO J. 8, 1735, (1989)]. The $\alpha 4\beta 7$ pairing is expressed on certain sub-populations of T and B lymphocytes and on eosinophils [Erle, D. J. et al, J. Immunol. 153, 517 (1994)]. Like $\alpha 4\beta 1$, $\alpha 4\beta 7$ binds to VCAM-1 and fibronectin. In addition, $\alpha 4\beta 7$ binds to an adhesion molecule believed to be involved in the homing of leukocytes to mucosal tissue termed MAdCAM-1 [Berlin, C. et al, Cell, 74, 185, (1993)]. The interaction between $\alpha 4\beta 7$ and MAdCAM-1 may also be important sites of inflammation outside of mucosal tissue [Yang, X.-D. et al, PNAS, 91, 12604, (1994)].

Regions of the peptide sequence recognizeded by $\alpha 4\beta 1$ and $\alpha 4\beta 7$ when they bind to their ligands have been identified. $\alpha 4\beta 1$ seems to recognise LDV, IDA or REDV peptide sequences in fibronectin and a QIDSP sequence in VCAM-1 [Humphries, M. J. et al, ibid] whilst $\alpha 4\beta 7$ recognises a LDT sequence in MAdCAM-1 [Birskin, M. J. et al, J. Immunol. 156, 719, (1996)]. There have been several reports of inhibitors of these interactions being designed from modifications of these short peptide sequences [Cardarelli, P. M. et al, J. Biol. Chem., 269, 18668, (1994); Shorff, H. N. et al, Biorganic Med. Chem. Lett., 6, 2495, (1996); Vanderslice, P. et al, J. Immunol., 158, 1710, (1997)]. It has also been reported that a short peptide sequence derived from the $\alpha 4\beta 1$ binding site in fibronectin can inhibit a contact hypersensitivity reaction in a trinitrochlorobenzene sensitised mouse [Ferguson, T. A., et al, PNAS, 88, 8072, (1991)].

Since the alpha 4 subgroup of integrins are predominantly expressed on leukocytes their inhibition can be expected to be beneficial in a number of immune or inflammatory disease states. However, because of the ubiquitous distribution and wide range of functions performed by other members of the integrin family it is important to be able to identify selective inhibitors of the alpha 4 subgroup.

We have now found a group of compounds which are potent and selective inhibitors of $\alpha 4$ integrins. Members of the group are able to inhibit $\alpha 4$ integrins such as $\alpha 4\beta 1$ and/or $\alpha 4\beta 7$ at concentrations at which they generally have no or minimal inhibitory action on $\alpha$ integrins of other subgroups. These compounds possess the additional advantage of good pharmacokinetic properties, especially low plasma clearance.

Thus according to one aspect of the invention we provide a compound of formula (1)

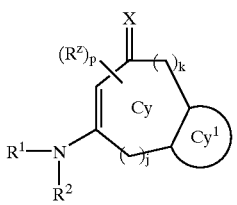

wherein
R$^1$ is a group Ar$^1$L$^2$Ar$^2$Alk- in which Ar$^1$ is an optionally substituted aromatic or heteroaromatic group, L$^2$ is a covalent bond or a linker atom or group, Ar$^2$ is an optionally substituted arylene or heteroarylene group and Alk is a chain —CH$_2$—CH(R)—, —CH=C(R)— or

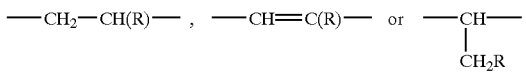

in which R is a carboxylic acid (—CO$_2$H) or a derivative or biostere thereof;
R$^2$ is a hydrogen atom or a C$_{1-6}$alkyl group;
X is an O or S atom or the group NR$^{30}$ in which R$^{30}$ is an optionally substituted aliphatic, heteroaliphatic, cycloaliphatic, heterocycloaliphatic, aromatic or hetero-aromatic group;
j and k is each zero or the integer 1 or 2 provided that the sum of j and k is zero or the integer 1 or 2;
Cy$^1$ is an optionally substituted cycloaliphatic, heterocycloaliphatic, aromatic or heteroaromatic group which incorporates two adjacent carbon atoms of the ring Cy within its ring structure such that the bond between these two atoms may be saturated or unsaturated.
R$^z$ which may be present on any available carbon atom of the ring Cy is selected from a halogen atom or -(Alk$^4$)$_v$L$^1$(Alk$^1$)$_n$(R$^3$)$_s$ atom or group in which Alk$^4$ is a straight or branched C$_{1-3}$alkylene chain, v is zero or the integer 1, L$^1$ is a covalent bond or a linker atom or group, n is zero or the integer 1, Alk$^1$ is an optionally substituted aliphatic chain, s is the integer 1, 2 or 3 and R$^3$ is a hydrogen atom or a —CN, —NO$_2$ or optionally substituted heteroaliphatic, cycloaliphatic, heterocycloaliphatic, polycycloaliphatic, heteropolycycloaliphatic, aromatic or heteroaromatic group provided that when v and n are zero and L$^1$ is a covalent bond s is the integer 1;
p is zero or the integer 1, 2 or 3;
and the salts, solvates, hydrates and N-oxides thereof.

It will be appreciated that compounds of formula (1) may have one or more chiral centres, and exist as enantiomers or diastereomers. The invention is to be understood to extend to all such enantiomers, diastereomers and mixtures thereof, including racemates. Formula (1) and the formulae hereinafter are intended to represent all individual isomers and mixtures thereof, unless stated or shown otherwise. In addition, compounds of formula (1) may exist as tautomers, for example keto (CH$_2$C=O)-enol (CH=CHOH) tautomers. Formula (1) and the formulae hereinafter are intended to represent all invidual tautomers and mixtures thereof unless stated otherwise.

Optionally substituted cycloaliphatic groups represented by the ring Cy$^1$ include optionally substituted C$_{3-10}$cycloaliphatic groups. Particular examples include optionally substituted C$_{3-10}$cycloalkyl e.g. C$_{3-7}$cycloalkyl or C$_{3-10}$cycloalkenyl e.g. C$_{3-7}$cycloalkenyl groups.

Particular examples of such cycloaliphatic groups include optionally substituted cyclopropyl, cyclobutyl, cyclopentyl, cyclohexyl, cycloheptyl, cyclobutenyl, cyclopentenyl, cyclohexenyl and cycloheptenyl groups.

Optionally substituted heterocycloaliphatic groups represented by the ring Cy$^1$ include optionally substituted C$_{3-10}$heterocycloaliphatic groups. Particular examples include optionally substituted C$_{3-10}$heterocycloalkyl, e.g. C$_{3-7}$heterocycloalkyl, or C$_{3-10}$heterocycloalkenyl, e.g. C$_{3-7}$heterocycloalkenyl groups, each of said groups containing one, two or three heteroatoms or heteroatom containing groups L$^5$ as defined hereinafter.

Particular examples of such heterocycloaliphatic groups include optionally substituted pyrrolinyl, pyrrolidinyl, oxazolinyl, oxazolidinyl, imidazolinyl, imidazolidinyl, pyrazolinyl, pyrazolidinyl, piperidinyl, morpholinyl, thiomorpholinyl and piperazinyl groups.

The optional substituents, R$^{20}$, which may be present on such cycloaliphatic and heterocycloaliphatic groups represented by the ring Cy$^1$ include those substituents described hereinafter in relation to R$^3$ cycloaliphatic and heterocycloaliphatic groups.

It will be appreciated that when a cycloalkenyl or heterocycloalkenyl group represented by the ring Cy$^1$ is fused to the ring Cy then the two adjacent carbon atoms that are common to both the ring Cy and the ring Cy$^1$ may be joined by a single bond (C—C) or a double bond (C=C).

Optionally substituted aromatic groups represented by the ring Cy$^1$ include optionally substituted phenyl groups.

Optionally substituted heteroaromatic groups represented by the ring Cy$^1$ include optionally substituted monocyclic C$_{2-5}$heteroaromatic groups containing for example one, two or three heteroatoms selected from oxygen, sulphur or nitrogen atoms. Monocyclic heteroaromatic groups include for example five- or six-membered heteroaromatic groups containing one, two or three heteroatoms selected from oxygen, sulphur or nitrogen atoms.

Particular examples of heteroaromatic groups of this type include pyrrolyl, furyl, thienyl, imidazolyl, oxazolyl, isoxazolyl, thiazolyl, isothiazolyl, pyrazolyl, 1,2,3-oxadiazolyl, 1,2,3-triazolyl, pyridyl, pyrimidinyl, pyridazinyl or pyrazinyl groups.

The optional substituents, R$^{20}$, which may be present on such aromatic and heteroaromatic groups include those substituents described hereinafter in relation to R$^3$ aromatic or heteroaromatic groups.

It will be appreciated that when an aromatic or heteroaromatic group represented by the ring Cy$^1$ is fused to the ring Cy then the two adjacent carbon atoms that are common to both the ring Cy and the ring Cy$^1$ will be joined by a double bond (C=C) in at least one tautomeric isomer of the aromatic or heteroaromatic group.

Particular non-limiting examples of ring structures formed by Cy—Cy¹ include:

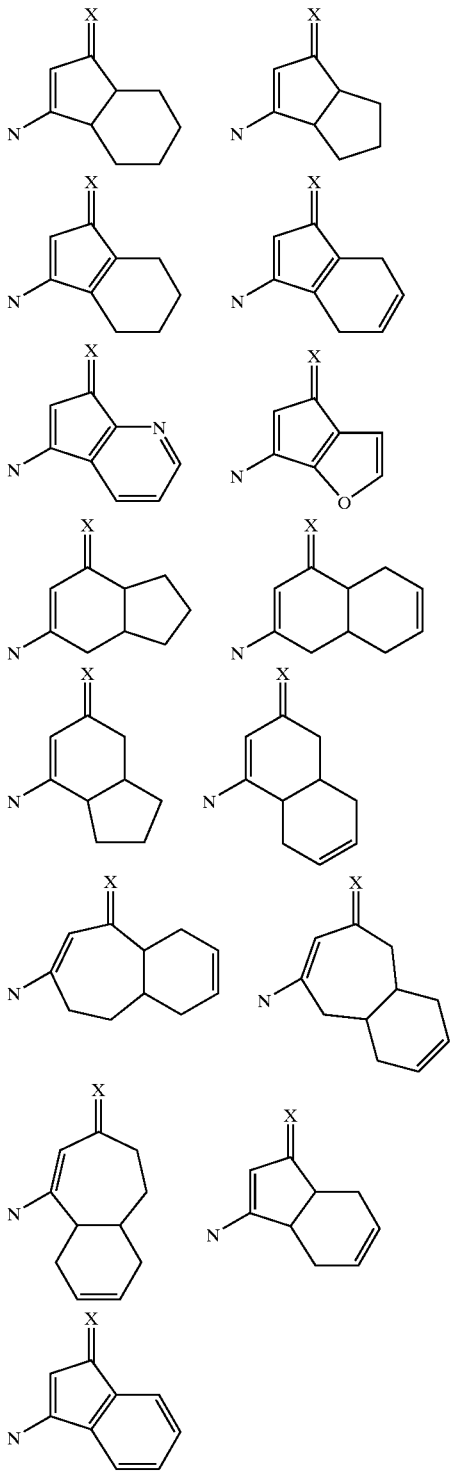

It will be understood that the invention extends to any possible combination of Cy and Cy¹ rings to give fused ring structures in a similar manner to the illustrated examples. It will be further understood that the N atom in the above ring structures is the N atom of the group NR¹R² in compounds of formula (1)

Optionally substituted aromatic groups represented by Ar¹ when present in the group R¹ include for example optionally substituted monocyclic or bicyclic fused ring $C_{6-12}$ aromatic groups, such as phenyl, 1- or 2-naphthyl, 1- or 2-tetrahydronaphthyl, indanyl or indenyl groups.

Optionally substituted heteroaromatic groups represented by the group Ar¹ when present in the group R¹ include for example optionally substituted $C_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example eight- to thirteen-membered fused-ring heteroaromatic groups containing one, two or more heteroatoms selected from oxygen, sulphur or nitrogen atoms.

Particular examples of heteroaromatic groups of these types include pyrrolyl, furyl, thienyl, imidazolyl, N-$C_{1-6}$alkylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, [2,3-dihydro]benzothienyl, benzothienyl, benzotriazolyl, indolyl, isoindolyl, benzimidazolyl, imidazo[1,2-a]pyridyl, benzothiazolyl, benzoxazolyl, benzopyranyl, [3,4-dihydro]benzopyranyl, quinazolinyl, quinoxalinyl, naphthyridinyl, e.g. 2,6-naphthyridinyl, pyrido[3,4-b]pyridyl, pyrido[3,2-b]pyridyl, pyrido[4,3-b]-pyridyl, quinolinyl, isoquinolinyl, tetrazolyl, 5,6,7,8-tetrahydroquinolinyl, 5,6,7,8-tetrahydroisoquinolinyl, and imidyl, e.g. succinimidyl, phthalimidyl, or naphthalimidyl such as 1,8-naphthalimidyl.

Each aromatic or heteroaromatic group represented by the group Ar¹ may be optionally substituted on any available carbon or, when present, nitrogen atom. One, two, three or more of the same or different substituents may be present and each substituent may be selected for example from an atom or group —$L^3(Alk^2)_tL^4(R^4)_u$ in which $L^3$ and $L^4$, which may be the same or different, is each a covalent bond or a linker atom or group, t is zero or the integer 1, u is an integer 1, 2 or 3, $Alk^2$ is an aliphatic or heteroaliphatic chain and $R^4$ is a hydrogen or halogen atom or a group selected from optionally substituted $C_{1-6}$alkyl or $C_{3-8}$ cycloalkyl, —OR⁵ [where R⁵ is a hydrogen atom, an optionally substituted $C_{1-6}$alkyl or $C_{3-8}$ cycloalkyl group], —SR⁵, —NR⁵R⁶ [where R⁶ is as just defined for R⁵ and may be the same or different], —NO₂, —CN, —CO₂R⁵, —SO₃H, —SOR⁵, —SO₂R⁵, —SO₃R⁵, —OCO₂R⁵, —CONR⁵R⁶, —OCONR⁵R⁶, —CSNR⁵R⁶, —COR⁵, —OCOR⁵, —N(R⁵)COR⁶, —N(R⁵)CSR⁶, —SO₂N(R⁵)(R⁶), —N(R⁵)SO₂R⁶, N(R⁵)CON(R⁶)(R⁷) [where R⁷ is a hydrogen atom, an optionally substituted $C_{1-6}$alkyl or $C_{3-8}$cycloalkyl group], —N(R⁵)CSN(R⁶)(R⁷) or —N(R⁵)SO₂N(R⁶)(R⁷), provided that when t is zero and each of $L^3$ and $L^4$ is a covalent bond then u is the integer 1 and R⁴ is other than a hydrogen atom.

When $L^3$ and/or $L^4$ is present in these substituents as a linker atom or group it may be any divalent linking atom or group. Particular examples include —O— or —S— atoms or —C(O)—, —C(O)O—, —OC(O)—, —C(S)—, —S(O)—, —S(O)₂—, —N(R⁸)— [where R⁸ is a hydrogen atom or an optionally substituted straight or branched $C_{1-6}$alkyl group], —CON(R⁸)—, —OC(O)N(R⁸)—, —CSN(R⁸)—, —N(R⁸)CO—, —N(R⁸)C(O)O—, —N(R⁸)CS—, —S(O)₂N(R⁸)—, —N(R⁸)S(O)₂—, —N(R⁸)O—, —ON(R⁸)—, —N(R⁸)N(R⁸)—, —N(R⁸)CON(R⁸)—, —N(R⁸)

CSN($R^8$)—, or —N($R^8$)SO$_2$N($R^8$)—groups. Where the linker group contains two $R^8$ substituents, these may be the same or different.

When $R^4$, $R^5$, $R^6$, $R^7$ and/or $R^8$ is present as a $C_{1-6}$alkyl group it may be a straight or branched $C_{1-6}$alkyl group, e.g. a $C_{1-3}$alkyl group such as a methyl or ethyl group. $C_{3-8}$cycloalkyl groups represented by $R^4$, $R^5$, $R^6$, $R^7$ and/or $R^8$ include $C_{3-6}$cycloalkyl groups e.g. cyclopropyl, cyclobutyl, cyclopentyl and cyclohexyl groups. Optional substituents which may be present on such groups include for example one, two or three substituents which may be the same or different selected from halogen atoms, for example fluorine, chlorine, bromine or iodine atoms, or hydroxy or $C_{1-6}$alkoxy e.g. methoxy or ethoxy groups.

When the groups $R^5$ and $R^6$ or $R^6$ and $R^7$ are both $C_{1-6}$alkyl groups these groups may be joined, together with the N atom to which they are attached, to form a heterocyclic ring. Such heterocyclic rings may be optionally interrupted by a further heteroatom selected from —O—, —S— or —N($R^5$)—. Particular examples of such heterocyclic rings include piperidinyl, morpholinyl, thiomorpholinyl, pyrrolidinyl, imidazolidinyl and piperazinyl rings.

When $Alk^2$ is present as an aliphatic or heteroaliphatic chain it may be for example any divalent chain corresponding to the below-mentioned aliphatic chains described for $Alk^1$ or heteroaliphatic groups described for $R^3$ where a terminal hydrogen atom is replaced by a bond.

Halogen atoms represented by $R^4$ in the optional $Ar^1$ substituents include fluorine, chlorine, bromine, or iodine atoms.

Examples of the substituents represented by —$L^3$($Alk^1$)$_t$ $L^4$($R^4$)$_u$ when present in $Ar^1$ groups in compounds of the invention include atoms or groups —$L^3Alk^2L^4R^4$, —$L^3Alk^2R^4$, —$L^3R^4$, —$R^4$ and —$Alk^2R^4$ wherein $L^3$, $Alk^2$, $L^4$ and $R^4$ are as defined above. Particular examples of such substituents include —$L^3CH_2L^4R^4$, —$L^3CH(CH_3)L^4R^4$, —$L^3CH(CH_2)_2L^4R^4$, —$L^3CH_2R^4$, —$L^3CH(CH_3)R^4$, —$L^3(CH_2)_2R^4$, —$CH_2R^4$, —$CH(CH_3)R^4$, —$(CH_2)_2R^4$ and —$R^4$ groups.

Thus $Ar^1$ in compounds of the invention may be optionally substituted for example by one, two, three or more halogen atoms, e.g. fluorine, chlorine, bromine or iodine atoms, and/or $C_{1-6}$alkyl, e.g. methyl, ethyl, n-propyl, i-propyl propyl, n-butyl or t-butyl, $C_{3-8}$cycloalkyl, e.g. cyclopropyl, cyclobutyl, cyclopentyl or cyclohexyl, $C_{1-6}$hydroxyalkyl, e.g. hydroxymethyl, hydroxyethyl or —C(OH)(CF$_3$)$_2$, carboxy$C_{1-6}$alkyl, e.g. carboxyethyl, $C_{1-6}$alkylthio e.g. methylthio or ethylthio, carboxy$C_{1-6}$alkylthio, e.g. carboxymethylthio, 2-carboxyethylthio or 3-carboxy-propylthio, $C_{1-6}$alkoxy, e.g. methoxy or ethoxy, hydroxy$C_{1-6}$alkoxy, e.g. 2-hydroxyethoxy, halo$C_{1-6}$alkyl, e.g. —CF$_3$, —CHF$_2$, CH$_2$F, halo$C_{1-6}$alkoxy, e.g. —OCF$_3$, —OCHF$_2$, —OCH$_2$F, $C_{1-6}$alkylamino, e.g. methylamino or ethylamino, amino (—NH$_2$), amino$C_{1-6}$alkyl, e.g. aminomethyl or aminoethyl, $C_{1-6}$dialkylamino, e.g. dimethylamino or diethylamino, $C_{1-6}$alkylamino$C_{1-6}$alkyl, e.g. ethylaminoethyl, $C_{1-6}$ dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, diisopropylaminoethoxy, or dimethylaminopropoxy, nitro, cyano, amidino, hydroxyl (—OH), formyl [HC(O)—], carboxyl (—CO$_2$H), —CO$_2$Alk$^3$ [where Alk$^3$ is as defined below for Alk$^8$], $C_{1-6}$alkanoyl e.g. acetyl, thiol (—SH), thio$C_{1-6}$alkyl, e.g. thiomethyl or thioethyl, sulphonyl (—SO$_3$H), —SO$_3$Alk$^3$, $C_{1-6}$alkylsulphinyl, e.g. methylsulphinyl, $C_{1-6}$alkylsulphonyl, e.g. methylsulphonyl, aminosulphonyl (—SO$_2$NH$_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, phenylaminosulphonyl, carboxamido (—CONH$_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, amino$C_{1-6}$alkylaminocarbonyl, e.g. aminoethylaminocarbonyl, $C_{1-6}$dialkylamino$C_{1-6}$alkylaminocarbonyl, e.g. diethylaminoethylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocabonyl$C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, aminosulphonylamino (—NHSO$_2$NH$_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, $C_{1-6}$alkanoylamino, e.g. acetylamino, amino$C_{1-6}$alkanoylamino e.g. aminoacetylamino, $C_{1-6}$dialkylamino$C_{1-6}$alkanoylamino, e.g. dimethylaminoacetylamino, $C_{1-6}$alkanoylamino$C_{1-6}$alkyl, e.g. acetylaminomethyl, $C_{1-6}$alkanoylamino$C_{1-6}$alkylamino, e.g. acetamidoethylamino, $C_{1-6}$alkoxycarbonylamino, e.g. methoxycarbonylamino, ethoxycarbonylamino or t-butoxycarbonylamino groups.

$L^2$ when present as part of the group $R^1$ in compounds of the invention may be a linker atom or group $L^{2a}$ or a linker group -(Alk$^a$)$L^{2a}$—, where Alk$^a$ is an optionally substituted aliphatic or heteroaliphatic chain as previously defined for Alk$^2$, and $L^{2a}$ is a linker atom or group as described above for $L^3$ and $L^4$.

Optionally substituted arylene groups represented by $Ar^2$ when present as part of the group $R^1$ include those aromatic groups as previously described for $Ar^1$.

Optionally substituted heteroarylene groups represented by $Ar^2$ when present as part of the group $R^1$ include those heteroaromatic groups as previously described for $Ar^1$.

Each arylene or heteroarylene group represented by $Ar^2$ may be attached to the remainder of the molecule through any available ring carbon or nitrogen atoms.

The arylene and heteroarylene groups represented by $Ar^2$ may be optionally substituted by one, two or more substituents selected from the atoms or groups —$L^3$(Alk$^2$)$_t$$L^4$(R$^4$)$_u$ described herein. Where two of these atoms or groups are present they may be the same or different.

When the group R is present in $R^1$ in compounds of the invention as a derivative of a carboxylic acid it may be for example a carboxylic acid ester or amide. Particular esters and amides include —CO$_2$Alk$^7$ and —CONR$^5$R$^6$ groups as defined herein. When R is a biostere of a carboxylic acid it may be for example a tetrazole or other acid such as phosphonic acid, phosphinic acid; sulphonic acid, sulphinic acid or boronic acid or an acylsulphonamide group.

Esters (—CO$_2$Alk$^7$) and amide (—CONR$^5$R$^6$) derivatives of the carboxylic acid group (—CO$_2$H) in compounds of formula (1) may advantageously be used as prodrugs of the active compound. Such prodrugs are compounds which undergo biotransformation to the corresponding carboxylic acid prior to exhibiting their pharmacological effects and the invention particularly extends to produgs of the acids of formula (1). Such prodrugs are well known in the art, see for example International Patent Application No. WO00/23419, Bodor, N. (Alfred Benzon Symposium, 1982, 17,156–177), Singh, G. et al (J. Sci. Ind. Res., 1996, 55, 497–510) and Bundgaard, H., (Design of Prodrugs, 1985, Elsevier, Amsterdam).

Esterified carboxyl groups represented by the group —CO$_2$Alk$^7$ wherein Alk$^7$ include groups is a straight or branched optionally substituted C$_{1-8}$alkyl group such as a methyl, ethyl, n-propyl, i-propyl, n-butyl, i-butyl, s-butyl or t-butyl group, an optionally substituted C$_{2-8}$alkenyl group such as a propenyl e.g. 2-propenyl or butenyl e.g. 2-butenyl or 3-butenyl group, an optionally substituted C$_{2-8}$alkynyl group such as a ethynyl, propynyl e.g. 2-propynyl or butynyl e.g. 2-butynyl or 3-butynyl group, an optionally substituted C$_{3-8}$cycloalkyl group such as a cyclopropyl, cyclobutyl, cyclopentyl, cyclohexyl or cycloheptyl group; an optionally substituted C$_{3-8}$cycloalkylC$_{1-8}$alkyl group such as a cyclopentylmethyl, cyclohexylmethyl or cyclohexylethyl group; an optionally substituted C$_{3-8}$heterocycloalkylC$_{1-6}$alkyl group such as a morpholinyl-N-ethyl, thiomorpholinyl-N-methyl, pyrrolidinyl-N-ethyl, pyrrolidinyl-N-propyl, piperidinyl-N-ethyl, pyrazolidinyl-N-methyl or piperazinyl-N-ethyl group; an optionally substituted C$_{1-6}$alkyloxyC$_{1-6}$alkyl group such as a methyloxyethyl or propyloxyethyl group; an optionally substituted C$_{1-6}$alkylthioC$_{1-6}$alkyl group such as an ethylthioethyl group; an optionally substituted C$_{1-6}$alkylsulfinylC$_{1-6}$alkyl group such as an methylsulfinylethyl group; an optionally substituted C$_{1-6}$alkylsulfonylC$_{1-6}$alkyl group such as an methylsulfonylmethyl group; an optionally substituted C$_{3-8}$cycloalkyloxyC$_{1-6}$alkyl group such as a cyclohexyloxymethyl group; an optionally substituted C$_{3-8}$cycloalkylthioC$_{1-6}$alkyl group such as a cyclopentylthiomethyl group; an optionally substituted C$_{3-8}$cycloalkylsulfinylC$_{1-6}$alkyl group such as a cyclopentylsulfinylmethyl group; an optionally substituted C$_{3-8}$cycloalkylsulfonylC$_{1-6}$alkyl group such as a cyclopentylsulfonylmethyl group; an optionally substituted C$_{1-6}$alkyloxycarbonylC$_{1-6}$alkyl group such as isobutoxycarbonylpropyl group; an optionally substituted C$_{1-6}$alkyloxycarbonylC$_{1-6}$alkenyl group such as isobutoxycarbonylpentenyl group; an optionally substituted C$_{1-6}$alkyloxycarbonyloxyC$_{1-6}$alkyl group such as an isopropoxycarbonyloxyethyl e.g a 1-(isopropoxycarbonyloxy)ethyl, 2-(isopropoxycarbonyloxy)ethyl or ethyloxycarbonyloxymethyl group; an optionally substituted C$_{1-6}$alkyloxycarbonyloxyC$_{1-6}$alkenyl group such as a isopropoxycarbonyloxybutenyl group, an optionally substituted C$_{3-8}$cycloalkyloxycarbonyloxyC$_{1-6}$alkyl group such as a cyclohexyloxycarbonyloxyethyl, e.g. a 2-(cyclohexyloxycarbonyloxy)ethyl group, an optionally substituted N-di-C$_{1-8}$alkylaminoC$_{1-8}$alkyl group such as a N-dimethylaminoethyl or N-diethylaminoethyl group; an optionally substituted N-C$_{6-12}$aryl-N-C$_{1-6}$alkylaminoC$_{1-6}$alkyl group such as a N-phenyl-N-methylaminomethyl group; an optionally substituted N-di-C$_{1-8}$alkylcarbamoylC$_{1-8}$alkyl group such as a N-diethylcarbamoylmethyl group; an optionally substituted C$_{6-10}$arylC$_{1-6}$alkyl group such as an optionally substituted benzyl, phenylethyl, phenylpropyl, 1-naphthylmethyl or 2-naphthylmethyl group; a C$_{6-10}$aryl group such as an optionally substituted phenyl, 1-naphthyl or 2-naphthyl group; a C$_{6-10}$aryloxyC$_{1-8}$alkyl group such as an optionally substituted phenyloxymethyl, phenyloxyethyl, 1-naphthyloxymethyl, or 2-naphthyloxymethyl group; a C$_{6-12}$arylthioC$_{1-8}$alkyl group such as an optionally substituted phenylthioethyl group; a C$_{6-12}$arylsulfinylC$_{1-8}$alkyl group such as an optionally substituted phenylsulfinylmethyl group; a C$_{6-12}$arylsulfonylC$_{1-8}$alkyl group such as an optionally substituted phenylsulfonylmethyl group; an optionally substituted C$_{1-8}$alkanoyloxyC$_{1-8}$alkyl group, such as a acetoxymethyl, ethoxycarbonyloxyethyl, pivaloyloxymethyl, propionyloxyethyl or propionyloxypropyl group; an optionally substituted C$_{4-8}$imidoC$_{1-8}$alkyl group such as a succinimidomethyl or phthalamidoethyl group; a C$_{6-12}$aroyloxyC$_{1-8}$alkyl group such as an optionally substituted benzoyloxyethyl or benzoyloxypropyl group or a triglyceride such as a 2-substituted triglyceride e.g. a 1,3-di-C$_{1-8}$alkylglycerol-2-yl group such as a 1,3-diheptylglycerol-2-yl group. Optional substituents present on the Alk$^7$ group include R$^{13a}$ substituents described above.

Optional substituents which may be present on the Alk$^7$ group include R$^{13a}$ substituents as defined hereinafter.

When the group R$^2$ is present in compounds of the invention as a C$_{1-6}$alkyl group it may be for example a straight or branched C$_{1-6}$alkyl group, e.g. a C$_{1-3}$alkyl group such as a methyl or ethyl group.

When the group R$^{30}$ is present in X in compounds of formula (1) as an aliphatic group it may be any aliphatic chain as described hereinafter for Alk$^1$ but with each containing a terminal hydrogen atom in place of one bond. When the group R$^{30}$ is present in compounds of formula (1) as a heteroaliphatic, cycloaliphatic, heterocycloaliphatic, aromatic or heteroaromatic group it may be any heteroaliphatic, cycloaliphatic, heterocycloaliphatic, aromatic or heteroaromatic group as described hereinafter for the group R$^3$. Optional substituents which may be present on these groups include those optional substituents described herein in relation to the corresponding Alk$^1$ aliphatic chains or R$^3$ heteroaliphatic, cycloaliphatic, heterocycloaliphatic, aromatic or heteroaromatic groups.

The group R$^z$ when present may be attached to any available carbon atom of the unsaturated ring represented by Cy.

C$_{1-3}$ alkylene chains represented by Alk$^4$ in the group R$^z$ in compounds of formula (1) include for example a —CH$_2$—, —CH$_2$CH$_2$—, —CH$_2$CH$_2$CH$_2$—, —CH(CH$_3$)CH$_2$— or —CH$_2$CH(CH$_3$)— chain.

When present the linker atom or group represented by L$^1$ in the group R$^z$ in compounds of formula (1) may be any linker atom or group as described above for the linker atom or group L$^3$.

When Alk$^1$ is present in the group R$^z$ in compounds of formula (1) as an optionally substituted aliphatic chain it may be an optionally substituted C$_{1-10}$ aliphatic chain. Particular examples include optionally substituted straight or branched chain C$_{1-6}$ alkylene, C$_{2-6}$ alkenylene, or C$_{2-6}$ alkynylene chains.

Particular examples of aliphatic chains represented by Alk$^1$ include optionally substituted —CH$_2$—, —(CH$_2$)$_2$—, —CH(CH$_3$)CH$_2$—, —(CH$_2$)$_2$CH$_2$—, —(CH$_2$)$_3$CH$_2$—, —CH(CH$_3$)(CH$_2$)$_2$—, —CH$_2$CH(CH$_3$)CH$_2$—, —C(CH$_3$)$_2$CH$_2$—, —CH$_2$C(CH$_3$)$_2$CH$_2$—, —(CH$_2$)$_2$C(CH$_3$)$_2$CH$_2$—, —(CH$_2$)$_4$CH$_2$—, —(CH$_2$)$_5$CH$_2$—, —CHCH—, —CHCHCH$_2$—, —CH$_2$CHCH—, —CHCHCH$_2$CH$_2$—, —CH$_2$CHCHCH$_2$—, —(CH$_2$)$_2$CHCH—, —CC—, —CCCH$_2$—, —CH$_2$CC—, —CCCH$_2$CH$_2$—, —CH$_2$CCCH$_2$— or —(CH$_2$)$_2$CCH— groups.

When s is the integer 2 or 3 each R$^3$ group, which may be the same or different, may be on the same or different carbon atoms of the aliphatic chain represented by Alk$^1$.

Heteroaliphatic groups represented by the group R$^3$ when present in the group R$^z$ in compounds of formula (1) include the aliphatic chains just described for Alk$^1$ but with each containing a terminal hydrogen atom and additionally containing one, two, three or four heteroatoms or heteroatom-containing groups. Particular heteroatoms or groups include atoms or groups L$^5$ where L$^5$ is as defined above for L$^3$ when L$^3$ is a linker atom or group. Each L$^5$ atom or group may interrupt the aliphatic group, or may be positioned at its terminal carbon atom to connect the group to an adjoining atom or group. Particular examples include optionally substituted —L$^5$CH$_3$, —CH$_2$L$^5$CH$_3$, —L$^5$CH$_2$CH$_3$, —CH$_2$L$^5$CH$_2$CH$_3$, —(CH$_2$)$_2$L$^5$CH$_3$, —(CH$_2$)$_3$L$^5$CH$_3$, —L$^5$(CH$_2$)$_3$, and —(CH$_2$)$_2$L$^5$CH$_2$CH$_3$ groups.

The optional substituents which may be present on aliphatic chains or heteroaliphatic groups represented by Alk$^1$ and R$^3$ respectively include one, two, three or more substituents where each substituent may be the same or different and is selected from halogen atoms, e.g. fluorine, chlorine, bromine or iodine atoms, or —OH, —CO$_2$H, —CO$_2$R$^9$, where R$^9$ is an optionally substituted straight or branched C$_{1-6}$alkyl group as defined above for R$^4$, —CONHR$^9$, —CON(R$^9$)$_2$, —COR$^9$, e.g. —COCH$_3$, C$_{1-6}$alkoxy, e.g. methoxy or ethoxy, thiol, —S(O)R$^9$, —S(O)$_2$R$^9$, C$_{1-6}$alkylthio e.g. methylthio or ethylthio, amino or substituted amino groups. Substituted amino groups include —NHR$^9$ and —N(R$^9$)$_2$ groups. Where two R$^9$ groups are present in any of the above substituents these may be the same or different.

Optionally substituted cycloaliphatic groups represented by the group R$^3$ when present in the group R$^z$ in compounds of the invention include optionally substituted C$_{3-10}$ cycloaliphatic groups. Particular examples include optionally substituted C$_{3-10}$ cycloalkyl, e.g. C$_{3-7}$ cycloalkyl or C$_{3-10}$ cycloalkenyl, e.g C$_{3-7}$ cycloalkenyl groups.

Optionally substituted heterocycloaliphatic groups represented by the group R$^3$ when present in the group R$^z$ include optionally substituted C$_{3-10}$heterocycloaliphatic groups. Particular examples include optionally substituted C$_{3-10}$heterocycloalkyl, e.g. C$_{3-7}$ heterocycloalkyl, or C$_{3-10}$heterocycloalkenyl, e.g. C$_{3-7}$ hetercycloalkenyl groups, each of said groups containing one, two, three or four heteroatoms or heteroatom-containing groups L$^5$ as defined above.

Optionally substituted polycycloaliphatic groups represented by the group R$^3$ when present in the group R$^z$ include optionally substituted C$_{7-10}$ bi- or tricycloalkyl or C$_{7-10}$bi- or tricycloalkenyl groups. Optionally substituted heteropolycycloaliphatic groups represented by the group R$^3$ include the optionally substituted polycycloalkyl groups just described, but with each group additionally containing one, two, three or four L$^5$ atoms or groups.

Particular examples of cycloaliphatic, polycycloaliphatic, heterocycloaliphatic and heteropolycycloaliphatic groups represented by the group R$^3$ include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, adamantyl, norbornyl, norbornenyl, tetrahydrofuranyl, pyrroline, e.g. 2- or 3-pyrrolinyl, pyrrolidinyl, pyrrolidinone, oxazolidinyl, oxazolidinone, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, pyranyl, e.g. 2- or 4-pyranyl, piperidinyl, piperidinone, 1,4-dioxanyl, morpholinyl, morpholinone, 1,4-dithianyl, thiomorpholinyl, piperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, e.g. o- or p-isoxazinyl, oxathiazinyl, e.g. 1,2,5 or 1,2,6-oxathiazinyl, or 1,3,5,-oxadiazinyl groups.

The optional substituents which may be present on the cycloaliphatic, polycycloaliphatic, heterocycloaliphatic or heteropolycycloaliphatic groups represented by the group R$^3$ include one, two, three or more substituents each selected from halogen atoms, e.g. fluorine, chlorine, bromine or iodine atoms, or C$_{1-6}$alkyl, e.g. methyl, ethyl or propyl, haloC$_{1-6}$alkyl, e.g. halomethyl or haloethyl such as difluoromethyl or trifluoromethyl, optionally substituted by hydroxyl, e.g. —C(OH)(CF$_3$)$_2$, C$_{1-6}$alkoxy, e.g. methoxy, ethoxy or propoxy, haloC$_{1-6}$alkoxy, e.g. halomethoxy or haloethoxy such as difluoromethoxy or trifluoromethoxy, thiol, C$_{1-6}$alkylthio e.g. methylthio, ethylthio or propylthio, or -(Alk$^{4a}$)$_g$R$^{10}$ groups in which Alk$^{4a}$ is a straight or branched C$^{1-3}$alkylene chain, g is zero or an integer 1 and R$^{10}$ is a —OH, —SH, —N(R$^{11}$)$_2$, (in which R$^{11}$ is an atom or group as defined herein for R$^8$) —CN, —CO$_2$R$^{11}$, —NO$_2$, —CON(R$^{11}$)$_2$, —CSN(R$^{11}$)$_2$, —COR$^{11}$, —CSN(R$^{11}$)$_2$, —N(R$^{11}$)COR$^{11}$, —N(R$^{11}$)CSR$^{11}$, —SO$_2$N(R$^{11}$)$_2$, —N(R$^{11}$)SO$_2$R$^{11}$, —N(R$^{11}$)CON(R$^{11}$)$_2$, —N(R$^{11}$)CSN (R$^{11}$), N(R$^{11}$)SO$_2$N(R$^{11}$)$_2$ or optionally substituted phenyl group. Where two R$^{11}$ atoms or groups are present in these substituents these may be the same or different. Optionally substituted phenyl groups include phenyl substituted by one, two or three of the R$^{13}$ groups described below.

Additionally, when the group R$^3$ is a heterocycloaliphatic group containing one or more nitrogen atoms each nitrogen atom may be optionally substituted by a group —(L$^6$)$_p$(Alk$^5$)$_q$R$^{12}$ in which L$^6$ is —C(O)—, —C(O)O—, —C(S)—, —S(O)$_2$—, —CON(R$^{11}$)—, —CSN(R$^{11}$)— or SO$_2$N(R$^{11}$)—; p is zero or an integer 1; Alk$^5$ is an optionally substituted aliphatic or heteroaliphatic chain; q is zero or an integer 1; and R$^{12}$ is a hydrogen atom or an optionally substituted cycloaliphatic, heterocycloaliphatic, polycycloaliphatic, heteropolycycloaliphatic, aromatic or heteroaromatic group.

C$_{1-3}$alkylene chains represented by Alk$^{4a}$ include those groups as previously described for Alk$^4$.

Optionally substituted aliphatic or heteroaliphatic chains represented by Alk$^5$ include those optionally substituted chains described above for Alk$^1$ and R$^3$ respectively. Optional substituents which may be present on these groups include those described above in relation to Alk$^1$ aliphatic chains.

Cycloaliphatic, heterocycloaliphatic, polycycloaliphatic or heteropolycycloaliphatic groups represented by R$^{12}$ include those groups just described for the group R$^3$. Optional substituents which may be present on those groups include those described above in relation to R$^3$ cycloaliphatic groups.

Aromatic or heteroaromatic groups represented by R$^{12}$ include those groups described herein for the group Ar$^1$. Optional substituents which may be present on these groups include those R$^{13}$ optional substituents described hereinafter.

When the group R$^3$ is an optionally substituted aromatic or heteroaromatic group it may be for example an aromatic or heteroaromatic group as described herein for the group Ar$^1$.

Optional substituents which may be present on the aromatic or heteroaromatic groups represented by the group $R^3$ include one, two, three or more substituents, each selected from an atom or group $R^{13}$ in which $R^{13}$ is —$R^{13a}$ or -$Alk^6(R^{13a})_m$, where $R^{13a}$ is a halogen atom, or an amino (—$NH_2$), substituted amino, nitro, cyano, amidino, hydroxyl (—OH), substituted hydroxyl, formyl, carboxyl (—$CO_2H$), esterified carboxyl, thiol (—SH), substituted thiol, —$COR^{14}$ [where $R^{14}$ is an -$Alk^6(R^{13a})_m$, aryl or heteroaryl group], —$CSR^{14}$, —$SO_3H$, —$SOR^{14}$, —$SO_2R^{14}$, —$SO_3R^{14}$, —$SO_2NH_2$, —$SO_2NHR^{14}$, —$SO_2N(R^{14})_2$, —$CONH_2$, —$CSNH_2$, —$CONHR^{14}$, —$CSNHR^{14}$, —$CON[R^{14}]_2$, —$CSN(R^{14})_2$, —$N(R^{11})SO_2R^{14}$, —$N(SO_2R^{14})_2$, —NH $(R^{11})SO_2NH_2$, —$N(R^{11})SO_2NHR^{14}$, —$N(R^{11})SO_2N(R^{14})_2$, —$N(R^{11})COR^{14}$, —$N(R^{11})CONH_2$, —$N(R^{11})CONHR^{14}$, —$N(R^{11})CON(R^{14})_2$, —$N(R^{11})CSNH_2$, —$N(R^{11})$ $CSNHR^{14}$, —$N(R^{11})CSN(R^{14})_2$, —$N(R^{11})CSR^{14}$, —$N(R^{11})$ $C(O)OR^{14}$, —$SO_2NHet^1$ [where -$NHet^1$ is an optionally substituted $C_{5-7}$cyclicamino group optionally containing one or more other —O— or —S— atoms or —$N(R^{11})$—, —C(O)—, —C(S)—, S(O) or —$S(O)_2$ groups], —$CONHet^1$, —$CSNHet^1$, —$N(R^{11})SO_2NHet^1$, —$N(R^{11})$ $CONHet^1$, —$N(R^{11})CSNHet^1$, —$SO_2N(R^{11})Het^2$ [where $Het^2$ is an optionally substituted monocyclic $C_{5-7}$carbocyclic group optionally containing one or more —O— or —S— atoms or —$N(R^{11})$—, —C(O)— or —C(S)— groups], -$Het^2$, —$CON(R^{11})Het^2$, —$CSN(R^{11})$ $Het^2$, —$N(R^{11})CON(R^{11})Het^2$, —$N(R^{11})CSN(R^{11})Het^2$, cycloaliphatic, heterocycloaliphatic, aryl or heteroaryl group; $Alk^6$ is a straight or branched $C_{1-6}$alkylene, $C_{2-6}$alkenylene or $C_{2-6}$alkynylene chain, optionally interrupted by one, two or three —O— or —S— atoms or —$S(O)_n$ [where n is an integer 1 or 2] or —$N(R^{15})$— groups [where $R^{15}$ is a hydrogen atom or $C_{1-6}$alkyl, e.g. methyl or ethyl group]; and m is zero or an integer 1, 2 or 3. It will be appreciated that when two $R^{11}$ or $R^{14}$ groups are present in one of the above substituents, the $R^{11}$ or $R^{14}$ groups may be the same or different.

When in the group -$Alk^6(R^{13a})_m$ m is an integer 1, 2 or 3, it is to be understood that the substituent or substituents $R^{13a}$ may be present on any suitable carbon atom in -$Alk^6$. Where more than one $R^{13a}$ substituent is present these may be the same or different and may be present on the same or different atom in -$Alk^6$. Clearly, when m is zero and no substituent $R^{13a}$ is present the alkylene, alkenylene or alkynylene chain represented by $Alk^6$ becomes an alkyl, alkenyl or alkynyl group.

When $R^{13a}$ is a substituted amino group it may be for example a group —$NHR^{14}$ [where $R^{14}$ is as defined above] or a group —$N(R^{14})_2$ wherein each $R^{14}$ group is the same or different.

When $R^{13a}$ is a halogen atom it may be for example a fluorine, chlorine, bromine, or iodine atom.

When $R^{13a}$ is a substituted hydroxyl or substituted thiol group it may be for example a group —$OR^{14}$ or a —$SR^{14}$ or —SC(=NH)$NH_2$ group respectively.

Esterified carboxyl groups represented by the group $R^{13a}$ include groups of formula —$CO_2Alk^8$ wherein $Alk^8$ is a straight or branched, optionally substituted $C_{1-8}$alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxyethyl, 1-naphthyloxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the $Alk^8$ group include $R^{13a}$ substituents described above.

When $Alk^6$ is present in or as a substituent it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —$S(O)_2$— or —$N(R^9)$— groups.

Cycloaliphatic or heterocycloaliphatic groups represented by the groups $R^{13a}$ or $R^{14}$ include those optionally substituted $C_{3-10}$cycloaliphatic or $C_{3-10}$heterocycloaliphatic groups described above for $R^3$.

Aryl or heteroaryl groups represented by the groups $R^{13a}$ or $R^{14}$ include mono- or bicyclic optionally substituted $C_{6-12}$ aromatic or $C_{1-9}$ heteroaromatic groups as described above for the group $Ar^1$. The aromatic and heteroaromatic groups may be attached to the remainder of the compound of formula (1) by any carbon or hetero e.g. nitrogen atom as appropriate.

When —$NHet^1$ or -$Het^2$ forms part of a substituent $R^{13}$ each may be for example an optionally substituted pyrrolidinyl, pyrazolidinyl, piperazinyl, morpholinyl, thiomorpholinyl, piperidinyl or thiazolidinyl group. Additionally $Het^2$ may represent for example, an optionally substituted cyclopentyl or cyclohexyl group. Optional substituents which may be present on —$NHet^1$ or -$Het^2$ include those $R^7$ substituents described above.

Particularly useful atoms or groups represented by $R^{13}$ include fluorine, chlorine, bromine or iodine atoms, or $C_{1-6}$alkyl, e.g. methyl, ethyl, n-propyl, i-propyl, n-butyl or t-butyl, optionally substituted phenyl, pyridyl, pyrimidinyl, pyrrolyl, furyl, thiazolyl, thienyl, morpholinyl, thiomorpholinyl, piperazinyl, e.g. t-butyloxycarbonylpiperazinyl, pyrrolidinyl, dioxolanyl, dioxanyl, oxazolidinyl, thiazolidinyl, imidazolidinyl or piperidinyl, $C_{1-6}$hydroxyalkyl, e.g. hydroxymethyl or hydroxyethyl, carboxy$C_{1-6}$alkyl, e.g. carboxyethyl, $C_{1-6}$alkylthio e.g. methylthio or ethylthio, carboxy$C_{1-6}$ alkylthio, e.g. carboxymethylthio, 2-carboxyethylthio or 3-carboxypropylthio, $C_{1-6}$alkoxy, e.g. methoxy or ethoxy, hydroxy$C_{1-6}$alkoxy, e.g. 2-hydroxyethoxy, optionally substituted phenoxy, pyridyloxy, thiazolyoxy, phenylthio or pyridylthio, $C_{4-7}$cycloalkyl, e.g. cyclobutyl, cyclopentyl, $C_{5-7}$cycloalkoxy, e.g. cyclopentyloxy, halo$C_{1-6}$alkyl, e.g. trifluoromethyl, halo$C_{1-6}$alkoxy, e.g. trifluoromethoxy, $C_{1-6}$alkylamino, e.g. methylamino, ethylamino or propylamino, C6–12arylC1–6alkylamino, e.g. benzylamino, 4-fluorobenzylamino or 4-hydroxyphenylethylamino, amino (—$NH_2$), amino$C_{1-6}$alkyl, e.g. aminomethyl or aminoethyl, $C_{1-6}$dialkylamino, e.g. dimethylamino or diethylamino, amino$C_{1-6}$alkylamino, e.g. aminoethylamino or aminopropylamino, optionally substituted $Het^1NC_{1-6}$ alkylamino, e.g. 3-morpholinopropylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, diisopropylaminoethoxy, or dimethylaminopropoxy, hydroxy$C_{1-6}$alkylamino, e.g. 2-hydroxyethylamino, 3-hydroxypropylamino or 3-hydroxybutylamino, imido, such as phthalimido or naphthalimido, e.g. 1,8- naphthalimido, nitro, cyano, amidino, hydroxyl (—OH), formyl [HC(O)—], carboxyl (—CO$_2$H), —CO$_2$Alk$^7$ [where Alk$^7$ is as defined above], C$_{1-6}$ alkanoyl e.g. acetyl, propyryl or butyryl, optionally substituted benzoyl, thiol (—SH), thioC$_{1-6}$alkyl, e.g. thiomethyl or thioethyl, —SC(=NH)NH$_2$, sulphonyl (—SO$_3$H), —SO$_3$Alk$^7$, C$_{1-6}$alkylsulphinyl, e.g. methylsulphinyl, ethylsulphinyl or propylsulphinyl, C$_{1-6}$alkylsulphonyl, e.g. methylsulphonyl, ethylsulphonyl or propylsulphonyl, aminosulphonyl (—SO$_2$NH$_2$), C$_{1-6}$alkylaminosulphonyl, e.g. methylaminosulphonyl, ethylaminosulphonyl or propylaminosulphonyl C$_{1-6}$dialkylaminosulphonyl, e.g. dimethylaminosulphonyl or diethylaminosulphonyl, phenylaminosulphonyl, carboxamido (—CONH$_2$), C$_{1-6}$alkylaminocarbonyl, e.g. methylaminocarbonyl, ethylaminocarbonyl or propylaminocarbonyl, C$_{1-6}$dialkylaminocarbonyl, e.g. dimethylaminocarbonyl or diethylaminocarbonyl, aminoC$_{1-6}$alkylaminocarbonyl, e.g. aminoethylaminocarbonyl, C$_{1-6}$alkylaminoC$_{1-6}$alkylaminocarbonyl, e.g. methylaminoethylaminocarbonyl, C$_{1-6}$dialkylaminoC$_{1-6}$alkylaminocarbonyl, e.g. diethylaminoethylaminocarbonyl, aminocarbonylamino, C$_{1-6}$alkylaminocarbonylamino, e.g. methylaminocarbonylamino or ethylaminocarbonylamino, C$_{1-6}$dialkylaminocarbonylamino, e.g. dimethylaminocarbonylamino or diethylaminocarbonylamino, C$_{1-6}$alkylaminocabonylC$_{1-6}$alkylamino, e.g. methylaminocarbonylmethylamino, aminothiocarbonylamino, C$_{1-6}$alkylaminothiocarbonylamino, e.g. methylaminothiocarbonylamino or ethylaminothiocarbonylamino, C$_{1-6}$dialkylaminothiocarbonylamino, e.g. dimethylaminothiocarbonylamino or diethylaminothiocarbonylamino, C$_{1-6}$alkylaminothiocarbonylC$_{1-6}$alkylamino, e.g. ethylaminothiocarbonylmethylamino, —CONHC(=NH)NH$_2$, C$_{1-6}$alkylsulphonylamino, e.g. methylsulphonylamino or ethylsulphonylamino, haloC$_{1-6}$alkylsulphonylamino, e.g. trifluoromethylsulphonylamino, C$_{1-6}$dialkylsulphonylamino, e.g. dimethylsulphonylamino or diethylsulphonylamino, optionally substituted phenylsulphonylamino, aminosulphonylamino (—NHSO$_2$NH$_2$), C$_{1-6}$alkylaminosulphonylamino, e.g. methylaminosulphonylamino or ethylaminosulphonylamino, C$_{1-6}$dialkylaminosulphonylamino, e.g. dimethylaminosulphonylamino or diethylaminosulphonylamino, optionally substituted morpholinesulphonylamino or morpholinesulphonylC$_{1-6}$alkylamino, optionally substituted phenylaminosulphonylamino, C$_{1-6}$alkanoylamino, e.g. acetylamino, aminoC$_{1-6}$alkanoylamino e.g. aminoacetylamino, C$_{1-6}$dialkylaminoC$_{1-6}$alkanoylamino, e.g. dimethylaminoacetylamino, C$_{1-6}$alkanoylaminoC$_{1-6}$alkyl, e.g. acetylaminomethyl, C$_{1-6}$alkanoylaminoC$_{1-6}$alkylamino, e.g. acetamidoethylamino, C$_{1-6}$alkoxycarbonylamino, e.g. methoxycarbonylamino, ethoxycarbonylamino or t-butoxycarbonylamino or optionally substituted benzyloxy, pyridylmethoxy, thiazolylmethoxy, benzyloxycarbonylamino, benzyloxycarbonylaminoC$_{1-6}$alkyl e.g. benzyloxycarbonylaminoethyl, thiobenzyl, pyridylmethylthio or thiazolylmethylthio groups.

Where desired, two R$^{13}$ substituents may be linked together to form a cyclic group such as a cyclic ether, e.g. a C$_{1-6}$alkylenedioxy group such as methylenedioxy or ethylenedioxy.

It will be appreciated that where two or more R$^{13}$ substituents are present, these need not necessarily be the same atoms and/or groups. In general, the substituent(s) may be present at any available ring position in the aromatic or heteroaromatic group represented by R$^3$.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isothionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

In the compounds according to the invention the group R$^1$ is preferably an Ar$^1$L$^2$Ar$^2$Alk- group. In compounds of this type Ar$^1$ is preferably an optionally substituted phenyl, monocyclic heteroaromatic or bicyclic heteroaromatic group. Particularly useful monocyclic heteroaromatic groups are optionally substituted five- or six-membered heteroaromatic groups as described previously, especially five- or six-membered heteroaromatic groups containing one or two heteroatoms selected from oxygen, sulphur or nitrogen atoms. Nitrogen-containing groups are especially useful, particularly pyridyl or pyrimidinyl groups. Particularly useful substituents present on these Ar$^1$ groups include halogen atoms or alkyl, haloalkyl, —OR$^5$, —SR$^5$, —NR$^5$R$^6$, —CO$_2$H, —CO$_2$CH$_3$, —NO$_2$, —N(R$^5$)COR$^6$ or —CN groups as described above in relation to the compounds of formula (1). Particularly useful bicyclic heteroaromatic groups represented by Ar$^1$ include optionally substituted ten-membered fused-ring heteroaromatic groups containing one or two heteroatoms, especially nitrogen atoms. Particular examples include optionally substituted naphthyridinyl, especially 2,6-naphthyridinyl and 2,7-naphthyridinyl, quinolinyl and isoquinolinyl, especially isoquinolin-1-yl groups. Particular optional substituents include those just described for monocyclic heteroaromatic groups.

A particularly useful group of compounds according to the invention has the formula (2a):

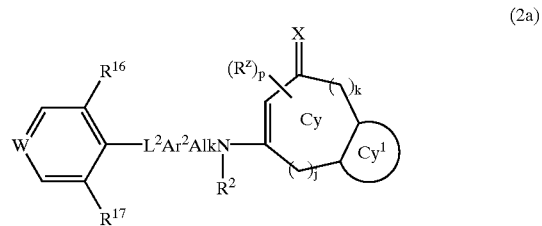

(2a)

wherein

—W= is —CH= or —N=;

R$^{16}$ and R$^{17}$, which may be the same or different is each a hydrogen atom or an atom or group —L$^3$(Alk$^2$)$_t$L$^4$(R$^4$)$_u$ in which L$^3$, Alk$^2$, t, L$^4$R$^4$ and u are as defined previously;

$L^2$, $Ar^2$, Alk, $R^2$, Cy, $Cy^1$, j, k, X, $R^z$ and p are as defined for formula (1);

and the salts, solvates, hydrates and N-oxides thereof.

In one particularly useful class of compounds of formula (2a) —W= is a —N= atom.

$R^{16}$ and $R^{17}$ in compounds of formula (2a) is each preferably as particularly described above for compounds of formula (1), other than a hydrogen atom. Particularly useful $R^{16}$ and $R^{17}$ substituents include halogen atoms, especially fluorine or chlorine atoms, or methyl, halomethyl, especially —$CF_3$, —$CHF_2$ or —$CH_2F$, methoxy or halomethoxy, especially —$OCF_3$, —$OCHF_2$ or —$OCH_2F$ groups. A most especially useful combination is that where $R^{16}$ and $R^{17}$ is each a halogen atom, especially a chlorine atom.

A further particularly useful group of compounds according to the invention has the formula (2b):

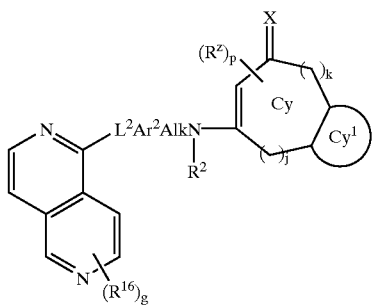
(2b)

wherein $R^{16}$, $L^2$, $Ar^2$, Alk, Cy, $R^2$, $Cy^1$, j, k, X, $R^z$ and p are as defined for formula (2a);

g is the integer 1, 2, 3 or 4;

and the salts, solvates, hydrates and N-oxides thereof.

Each $R^{16}$ atom or group in compounds of formula (2b) may be independently selected from an atom or group —$L^3(Alk^2)_tL^4(R^4)_u$ in which $L^2$, $Alk^2$, t, $L^3$, $R^4$ and u are as previously defined. Particularly useful $R^{16}$ substituents when present in compounds of formula (2b) include halogen atoms, especially fluorine or chlorine atoms, or straight or branched $C_{1-6}$alkyl, especially methyl, ethyl or isopropyl, $C_{3-8}$cycloalkyl especially cyclopropyl, halo$C_{1-6}$alkyl, especially halomethyl, most especially —$CF_3$ or —$CHF_2$, straight of branched $C_{1-6}$alkoxy, especially methoxy or ethoxy, halo$C_{1-6}$alkoxy, especially halomethoxy, most especially —$OCF_3$ or —$OCHF_2$, —$SR^5$ especially methylthio or ethylthio, —CN, —$CO_2Alk^3$, especially —$CO_2CH_3$, —$NO_2$, amino (—$NH_2$), substituted amino (—$NR^5R^6$), —$N(R^5)COR^6$, especially —$NHCOCH_3$, —$COR^5$, especially —$COCH_3$, optionally substituted $C_{6-12}$aromatic, especially optionally substituted phenyl and $C_{1-9}$heteroaromatic groups, especially optionally substituted thienyl, pyridyl and pyrimidinyl groups.

A further particularly useful group of comounds according to the invention has the formula (2c):

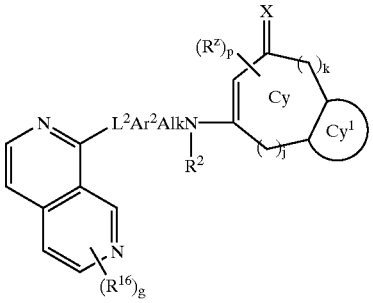
(2c)

Wherein $R^{16}$, g, $L^2$, $Ar^2$, $R^2$, Cy, $Cy^1$, j, k, X, $R^z$ and p are as defined for formula (2b);

and the salts solvates, hydrates and N-oxides thereof.

Each $R^{16}$ atom or group in compounds of formula (2c) may be independently selected from an atom or group —$L^3(Alk^2)_tL^4(R^4)_u$ as previously described for compounds of formula (2b).

In one particularly preferred class of compounds of formula (2c) g is zero.

In another particularly preferred class of compounds of formula (2c) 9 is the integer 1 or 2.

An especially preferred class of compounds of formula (2c) is that where g is the integer 1 and $R^{16}$ is a substituent at the 3-position of the 2,7-naphthyridine ring. In this class of compounds $R^{16}$ is most preferably a methyl or halomethyl, especially —$CF_3$ group, or an optionally substituted phenyl group.

Particularly useful optional substituents which may be present on $R^{16}$ aromatic and heteroaromatic groups when present in compounds of formula (2b) or (2c) include halogen atoms, especially fluorine and chlorine atoms, $C_{1-6}$alkyl groups, especially fluorine and chlorine atoms, $C_{1-6}$alkyl groups, especially methyl, ethyl and i-propyl groups and —$CF_3$, —$OCH_3$, —$OCH_2CH_3$, —$OCH(CH_3)_2$, —$OCF_3$, —$SCH_3$, —$NHCH_3$, —$N(CH_3)_2$, —CN, —$CO_2CH_3$, —$COCH_3$, and —$N(CH_3)COCH_3$ groups.

A further particularly useful group of compounds according to the invention has the formula (2d):

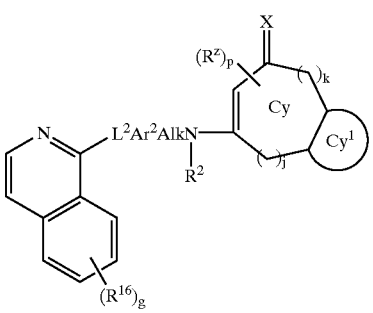
(2d)

wherein $R^{16}$, g, $L^2$, $Ar^2$, Alk, $R^2$, Cy, $Cy^1$, j, k, X, $R^z$ and p are as defined for formula (2b);

and the salts, solvates, hydrates and N-oxides thereof.

Each $R^{16}$ atom or group in compounds of formula (2c) may be independently selected from an atom or group —$L^3(Alk^2)_tL^4(R^4)_u$ as previously defined for compounds of formula (2b).

In one preferred class of compounds of formula (2d) g is zero.

In another preferred class of compounds of formula (2d) g is the integer 1. In this class of compounds $R^{16}$ is preferably a substituent at the 3-positions of the isoquinoline ring as just defined. Most especially useful $R^{16}$ substituents of this type include halogen atoms, especially fluorine and chlorine atoms and straight or branched $C_{1-6}$alkyl groups, especially methyl, ethyl or isopropyl, most especially methyl groups or optionally substituted phenyl, thienyl or pyridyl groups, where preferred optional substituents include those groups as hereinbefore described in relation to $R^{16}$ aromatic groups in compounds of formula (2b).

In another preferred class of compounds of formula (2d) g is the integer 2 or 3 where one $R^{16}$ group is as just generally and particularly defined, and is located at the 3-position of the isoquinoline ring. In this class of compounds the second and when present third $R^{16}$ optional substituents may be selected from an $R^{16}$ optional substituent as described for compounds of formula (2b) or when g is the integer 3 a $C_{1-6}$alkylenedioxy group, especially a methylenedioxy or ethylenedioxy group. In one particularly useful group of compounds of this class g is the integer 2 where one $R^{16}$ group is at the 3-position of the isoquinoline ring as previously generally and particularly described and the other $R^{16}$ group is at the 6-, 7- or 8-position of the isoquinoline ring, most especially the 7-position. Most especially preferred substituents at the 7-position include a halogen atom, especially a fluorine or chlorine atom, or a $C_{1-6}$alkoxy group, especially a methoxy group.

It will be understood that compounds according to formulae (2a), (2b), (2c) and (2d) include, where applicable, the corresponding hydroxy tautomers.

Alk in compounds of the invention is preferably:

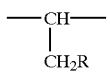

or, especially, —$CH_2CH(R)$—.

In one preferred class of compounds of formulae (1), (2a), (2b), (2c) and (2d) $R^2$ is a hydrogen atom.

In another preferred class of the compounds of formulae (1), (2a), (2b), (2c) and (2d) R is preferably a —$CO_2H$ group.

In a further preferred class of compounds of formulae (1) and (2) R is an esterified carboxyl group of formula —$CO_2Alk^7$. In this class of compound $Alk^7$ is preferably a $C_{1-8}$alkyl group, especially a methyl, ethyl, propyl or i-propyl group, an optionally substituted $C_{6-10}$aryl group, especially a phenyl group, an optionally substituted $C_{6-10}$aryl$C_{1-6}$alkyl group, especially a benzyl group, a $C_{3-8}$heterocycloalkyl$C_{1-6}$alkyl group, especially a morpholinyl-N-ethyl group or a $C_{1-6}$alkyloxy$C_{1-6}$alkyl group, especially a methyloxyethyl group. Especially preferred esterified carboxyl groups include —$CO_2CH_3$, —$CO_2CH_2CH_3$, —$CO_2CH_2CH_2CH_3$ and —$CO_2CH(CH_3)_2$ groups.

In general in compounds of formula (2a) when W is a —N= atom, $L^2$ is preferably $L^{2a}$ where $L^{2a}$ is a —CON ($R^8$)— group, especially —CONH— or -(Alk$^a$)$L^{2a}$— where -(Alk$^a$)$L^{2a}$— is especially a —$CH_2O$— group. Most preferred is a —CONH— group.

In general in compounds of formula (2a) when W is a —CH=group $L^2$ is preferably a covalent bond or $L^{2a}$ where $L^{2a}$ is a —CON(R)$^8$— group, especially —CONH— or -(Alk$^a$)$L^{2a}$— where -(Alk$^a$)$L^{2a}$— is especially a —$CHO_2O$— group. When W in compounds of formula (2a) is a —CH=group $L^2$ is most preferably a covalent bond.

In general in compounds of formula (2b), (2c) and (2d) $L^2$ is preferably $L^{2a}$ where $L^{2a}$ is an —O— atom or —N(R$^8$)— group. An especially useful —N(R$^8$)— group is —NH—.

The group $Ar^2$ in compounds of formulae (1), (2a), (2b), (2c) and (2d) is preferably an optionally substituted phenylene group. Particularly useful groups include optionally substituted 1,4-phenylene groups.

In one preferred class of compounds of formulae (1), (2a), (2b), (2c) and (2d) i and k is each zero, p is zero or the integer 1 and Cy—Cy$^1$ has the formula (2e):

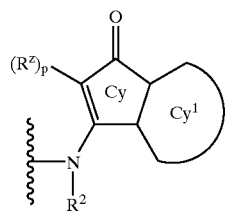

(2e)

In this class of compounds the ring Cy$^1$ is preferably an optionally substituted cycloaliphatic or heterocycloaliphatic group. Particularly useful cycloaliphatic groups include optionally substituted $C_{3-7}$cycloalkyl and $C_{3-7}$cycloalkenyl groups. Especially useful optionally substituted $C_{3-7}$cycloalkyl groups include optionally substituted cyclopentyl and cyclohexyl groups. Especially useful optionally substituted $C_{3-7}$cycloalkenyl groups include optionally substituted cyclopentenyl and cyclohexenyl groups where the double bond may be betweeen any two carbon atoms of the Cy$^1$ ring.

Particularly useful heterocycloaliphatic groups represented by Cy$^1$ in compounds of formula (2e) include optionally substituted $C_{3-7}$heterocycloalkyl and $C_{3-7}$heterocycloalkenyl groups especially optionally substituted pyrrolidinyl, piperidinyl and piperazinyl groups where one or two of the non ring-fused carbon atoms of the ring Cy$^1$ is replaced by an NH group.

In another preferred class of compound of formula (1), (2a) (2b), (2c) and (2d) j is the integer 1 and k is zero or k is the integer 1 and j is zero, p is zero or the integer 1 or 2 and Cy—Cy$^1$ has the formula (2f) or (2 g):

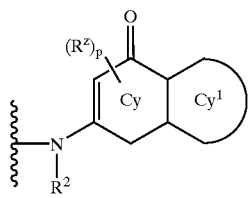

(2f)

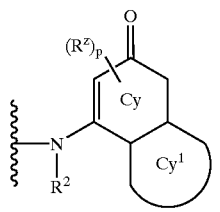

(2g)

In this class of compound the ring Cy$^1$ is preferably an optionally substituted cycloaliphatic or heterocycloaliphatic group. Particularly useful cycloaliphatic groups include $C_{3-7}$cycloalkyl and $C_{3-7}$cycloalkenyl rings, especially optionally substituted cyclopentyl, cyclohexyl, cyclopentenyl and cyclohexenyl rings.

Particularly useful heterocycloaliphatic groups include optionally substituted $C_{3-7}$heterocycloalkyl and $C_{3-7}$heterocycloalkenyl groups, especially optionally substituted pyrrolidinyl, piperidinyl and piperazinyl rings where one or two of the non ring-fused carbon atoms of the ring $Cy^1$ is replaced by an NH group.

In compounds of formula (2f) and (2 g) when p is the integer 1 or 2 the/one of the $R^2$ groups is preferably attached to the double bond carbon adjacent to the carbonyl group of the ring Cy.

In another preferred class of compounds of formula (1), (2a), (2b), (2c) and (2d) p is zero or the integer 1 or 2 and Cy—$Cy^1$ has the structure (2e), (2f) or (2 g). In this class of compounds the ring $Cy^1$ is preferably an optionally substituted phenyl or pyridyl group. When $Cy^1$ is a pyridyl group the pyridyl N atom may be at any non-bridgehead position of the ring $Cy^1$. Particularly useful optional substituents which may be present on phenyl and pyridyl groups include halogen atoms, especially fluorine or chlorine atoms or $C_{1-6}$alkyl especially methyl, ethyl or isopropyl, halo$C_{1-6}$alkyl such as halomethyl, especially —$CF_3$, —$CHF_2$ or —$CH_2F$, $C_{1-6}$alkoxyl especially methoxy, ethoxy or isopropoxy, halo$C_{1-6}$alkyl such as or halomethoxy, especially —$OCF_3$, —$OCHF_2$ or —$OCH_2F$, $C_{1-6}$alkylenedioxy, especially methylenedioxy, substituted amino (—$NHR^{14}$, —$N(R^{14})_2$) especially —$NHCH_3$ and —$N(CH_3)_2$, nitro (—$NO_2$), nitrile (—CN) and esterified carboxyl (—$CO_2Alk^7$) especially —$CO_2CH_3$ groups.

It will be understood that the corresponding hydroxy (—OH) tautomers of those oxo (=O) containing Cy rings, where the double bond migrates to become part of the Cy ring structure are also included in the definition or preferred Cy rings.

In general in compounds of formulae (1), (2a), (2b), (2c) and (2d) p is preferably zero or the integer 1 or 2.

In general in compounds of formulae (1), (2a), (2b), (2c) and (2d) when v and n in the group $R^z$ are zero or the integer 1 the group $R^3$ may especially be an optionally substituted heteroaliphatic, cycloaliphatic, heterocycloaliphatic, aromatic or heteroaromatic group as defined herein. Particularly useful groups of this type include optionally substituted $C_{2-6}$heteroalkyl, particularly $C_{1-3}$alkoxy$C_{1-3}$alkyl, especially methoxypropyl, optionally substituted $C_{3-7}$cycloalkyl, especially optionally substituted cyclopropyl, cyclobutyl cyclopentyl or cyclohexyl, optionally substituted $C_{5-7}$heterocycloaliphatic, optionally substituted pyrrolidinyl or thiazolidinyl, optionally substituted phenyl and optionally substituted $C_{5-7}$heteroaromatic, especially optionally substituted pyridyl groups. Optional substituents on these groups include in particular $R^{13}$ atoms or groups where the group is an aromatic or heteroaromatic group and —$(L^6)_p(Alk^5)_qR^{12}$ groups as described earlier where the group is a nitrogen-containing heterocycloaliphatic group such as a pyrrolidinyl or thiazolidinyl group. Particularly useful —$(L^6)_p(Alk^5)_q$ $R^{12}$ groups include those in which $L^6$ is a —CO— group. $Alk^5$ in these groups is preferably present (i.e. q is preferably an integer 1) and in particular is a —$CH_2$— chain. Compounds of this type in which $R^{12}$ is a hydrogen atom or an optionally substituted aromatic or heteroaromatic group, especially an optionally substituted phenyl, pyridyl or imidazolyl group are particularly preferred.

In one preferred class of compounds of formulae (1), (2a), (2b), (2c) and (2d) v in the group $R^z$ is zero and $L^1$ is present as a —$N(R^8)$— group. Particularly useful —$N(R^8)$— groups include —NH—, —$N(CH_3)$—, —$N(CH_2CH_3)$— and —$N(CH_2CH_2CH_3)$— groups.

In another preferred group of compounds of formulae (1), (2a), (2b), (2c) and (2d) v is zero, $Alk^1$ in the group $R^z$ is present as an aliphatic chain as defined herein (i.e. n is the integer 1), s is the integer 1 and $R^3$ is a hydrogen atom. Compounds of this type where -$Alk^1R^3$ is an optionally substituted $C_{1-6}$alkyl group, particularly a methyl, ethyl, n-propyl i-propyl, i-butyl, t-butyl, n-butyl, or an allyl (—$CH_2CHCH_2$) or propargyl (—$CH_2CCH$) group are especially useful. In one preferred class of compounds of this type $L^1$ is a covalent bond. In another preferred class of compounds of this type $L^1$ is a group —$N(R^8)$— as previously generally and particularly defined.

Particularly preferred optional substituents which may be present on aliphatic groups of formula -$Alk^1R^3$ include one, two, three or more halogen atoms, esepcially fluorine, chlorine or bromine atoms or $C_{1-6}$alkoxy groups e.g. methoxy or ethoxy, halo$C_{1-6}$alkoxy groups e.g. —$OCF_3$, substituted amino groups e.g. —$NHCH_3$ or —$N(CH_3)_2$ or —$COR^9$ groups e.g. —$COCH_3$ or carboxyl (—$CO_2H$) or esterified carboxyl e.g. —$CO_2CH_3$ or —$CO_2C(CH_3)_2$ groups.

In one most preferred class of compounds of formulae (1), (2a), (2b), (2c) and (2d) p is the integer 1 and $R^z$ is an optionally substituted aliphatic group -$Alk^1R^3$ as just defined.

Particularly useful compounds of the invention include:

(2S)-3-[4-(2,6-Naphthyridin-1-ylamino)phenyl]-2-[(1-oxo-3a,4,7,7a-tetrahydro-1H-inden-3-yl)amino]propionic acid;

(2S)-3-[4-(2,7-Naphthyridin-1-ylamino)phenyl]-2-[(1-oxo-2-propyl)-3a,4,5,6,7,7a-hexahydro-1-H-inden-3-yl) amino]propionic acid;

and the salts, solvates, hydrates, N-oxides and carboxylic acid ester, particularly methyl, ethyl, propyl and 2-propyl esters thereof.

Compounds according to the invention are potent and selective inhibitors of α4 integrins. The ability of the compounds to act in this way may be simply determined by employing tests such as those described in the Examples hereinafter.

The compounds are of use in modulating cell adhesion and in particular are of use in the prophylaxis and treatment of diseases or disorders including inflammation in which the extravasculation of leukocytes plays a role and the invention extends to such a use and to the use of the compounds for the manufacture of a medicament for treating such diseases or disorders in a mammal, especially a human.

Diseases or disorders of this type include inflammatory arthritis such as rheumatoid arthritis vasculitis or polydermatomyositis, multiple sclerosis, allograft rejection, diabetes, inflammatory dermatoses such as psoriasis or dermatitis, asthma and inflammatory bowel disease.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols $Ar^1$, $Ar^2$, Alk, $R^1$, $R^2$, $R^3$, $L^1$, $L^2$, $Alk^1$, Cy, $Cy^1$, X, j, k, $R^z$, p and n when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1999]. In some instances, deprotection may be the final step in the synthesis of a compound of formula (1) and the processes according to the invention described hereinafter are to be understood to extend to such removal of protecting groups. For convenience the processes described below all refer to a preparation of a compound of formula (1) but clearly the description applies equally to the preparation of compounds of formula (2).

Thus according to a further aspect of the invention, a compound of formula (1) in which R is a —$CO_2H$ group may be obtained by hydrolysis of an ester of formula (3):

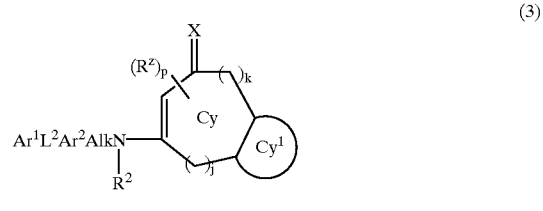

(3)

where Alk represents a group
—$CH_2CH(CO_2Alk^{10})$—, —$CH$=$CH(CO_2Alk^{10})$—, or

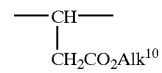

[where $Alk^{10}$ is an alkyl group for example a $C_{1-6}$alkyl group]

The hydrolysis may be performed using either an acid or a base depending on the nature of $Alk^{10}$, for example an organic acid such as trifluoroacetic acid or an inorganic base such as lithium, sodium or potassium hydroxide optionally in an aqueous organic solvent such as an amide e.g. a substituted amide such as dimethylformamide, an ether e.g. a cyclic ether such as tetrahydrofuran or dioxane or an alcohol e.g. methanol at a temperature from ambient to the reflux temperature. Where desired, mixtures of such solvents may be used.

According to a further aspect of the invention a compound of formula (1) may be prepared by condensation of a compound of formula (4):

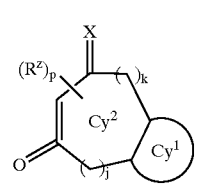

(4)

where $Cy^2$ is a cycloaliphatic ring in which the double bond of the Cy ring of compounds of formula (1) is replaced by a single bond and an oxo (=O) substituent is attached to the carbon atom to which $R^1R^2N$— will subsequently be joined, with an amine $R^1R^2NH$ or a salt thereof.

The reaction may be performed in an inert solvent or mixture of solvents, for example a hydrocarbon such as an aromatic hydrocarbon e.g. benzene or toluene and/or a halogenated hydrocarbon such as 1,2-dichloroethane, at a temperature from 0° C. to the reflux temperature. Where necessary, for example when a salt of an amine $R^1R^2NH$ is used, an organic base such as diisopropylethylamine can be added.

Any carboxylic acid group present in the intermediate of formula (4) or the amine $R^1R^2NH$ may need to be protected during the displacement reaction, for example as an ethyl ester. The desired acid may then be obtained through subsequent hydrolysis, for example as particularly described above and generally described below.

Compounds of formula (4) may be prepared by well known methods in the art e.g. the methods of Mosher, W. A. et al [J. Org. Chem. 37, 3190–2 (1972)], Hamer, N. K. [Tetrahedron Lett. 27, 2167–8 (1986)], Gandhi, P. [Chem. Ind. 290–1 (1980)] Umehara, M. et al [Bull Chem. Soc. Jpn. 60, 4474–6 (1987)] and Dallemange, P. et al [An. Quim. 88, 130–2 (1992)].

A compound of formula (1) may also be prepared by displacement of a leaving group from a compound of formula (5):

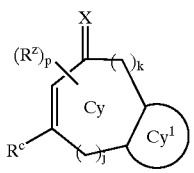

(5)

where $R^c$ is a leaving group, with an amine $R^1R^2NH$ or a salt thereof. Suitable leaving groups represented by $R^c$ include a halogen atom especially a chlorine, bromine or iodine atom, or alkoxy e.g. methoxy or ethoxy or isopropyloxy, alkylthio e.g. methylthio or ethylthio, alkyl-sulphoxide e.g. methylsulphoxide, aryloxy e.g. dinitrophenyloxy or araalkoxy e.g. benzyloxy group.

The reaction may be performed in an inert solvent or mixture of solvents for example a substituted amide such as dimethylformamide, or alcohol such as methanol or ethanol and/or a halogenated hydrocarbon such as dichloromethane, at a temperature from 0° C. to the reflux temperature. Where necessary, for example when the salt of an amine $R^1R^2NH$ is used an organic base such as diisopropylethylamine can be added.

Compounds of formula (5) may be prepared by well known in the art e.g. the methods of Heffner R. J. et al [Synth. Commun. 21, 2231–56 (1991)], Balsells J. et al [Org. Lett. 1981–84 (1999)], Chorvat, J. et al [J. Heterocyclic Chem. 17, 1313–15 (1980)], Moehrle, H. et al [Chem.-Ztg. 106, 19 (1982)] and Krafft, G. et al [J. Am. Chem. Soc. 103, 5459–66 (1981)].

Where desired the displacement reaction may also be performed on an intermediate of formulae (4) or (5) or $R^1R^2NH$ which is linked, for example via its $R^1$ or $R^3$ group, to a solid support, such as a polystyrene resin. After the reaction the desired compound of formula (1) may be displaced from the support by any convenient method, depending on the original linkage chosen.

Intermediates of formulae (4), (5) and $R^1R^2NH$ may be obtained from simpler, known compounds by one or more standard synthetic methods employing substitution, oxidation, reduction or cleavage reactions. Particular substitution approaches include conventional alkylation, arylation, heteroarylation, acylation, thioacylation, halogenation, sulphonylation, nitration, formylation and coupling procedures. It will be appreciated that these methods may also be used to obtain or modify other compounds of formulae (1) and (2) where appropriate functional groups exist in these compounds.

Thus compounds of the invention and intermediates thereto may be prepared by alkylation, arylation or heteroarylation. For example, compounds containing a —$L^1H$ or —$L^2H$ group (where $L^1$ and $L^2$ is each a linker atom or group) may be treated with a coupling agent $R^3(Alk^1)_nX^1$ or $Ar^1X^1$ respectively in which $X^1$ is a leaving atom or group such as a halogen atom, e.g. a fluorine, bromine, iodine or chlorine atom or a sulphonyloxy group such as an alkylsulphonyloxy, e.g. trifluoromethylsulphonyloxy or arylsulphonyloxy, e.g. p-toluene-sulphonyloxy group.

The reaction may be carried out in the presence of a base such as a carbonate, e.g. caesium or potassium carbonate, an alkoxide, e.g. potassium t-butoxide, or a hydride, e.g. sodium hydride, or an organic amine e.g. triethylamine or N,N-diisopropylethylamine or a cyclic amine, such as N-methylmorpholine or pyridine, in a dipolar aprotic solvent such as an amide, e.g. a substituted amide such as dimethylformamide or an ether, e.g. a cyclic ether such as tetrahydrofuran.

Compounds of formula $Ar^1X^1$ in which, for example, $Ar^1$ represents a 2,6-naphthyridine may be prepared from alcohols of formula $Ar^1OH$ by reaction with a halogenating agent, for example a phosphorous oxyhalide such as phosphorous oxychloride at an elevated temperature e.g. 110° C.

Intermediate alcohols of formula $Ar^1OH$ in which, for example, $Ar^1$ represents a 2,6-naphthyridine may be prepared by methods well known to a person skilled in the art, e.g. by the method of Sakamoto, T. et al [Chem. Pharm. Bull. 33, 626–633, (1985)]. Similarly intermediates of formula ArOH in which $Ar^1$ represents a 2,7-naphthyridine may be prepared by the method of Baldwin, J. et al [J. Org. Chem. 43 4878–4880, (1978)] and where $Ar^1$ represents an isoquinoline by the methods of Wu M.-J. et al [Tetrahedron, 55, 13193–200 (1999)], Hiebl J. et al [Tetrahedron, Lett. 40, 7935–38 (1999)] and Brun E. M. et al [Synlett, 7, 1088–90 (1999)].

Alternatively alkylating agents of formula $Ar^1X^1$ in which, for example, $Ar^1$ represents a 2,6-naphthyridine may be prepared by reaction of a 2,6-naphthyridine N-oxide or N,N'-dioxide with a halogenating agent, e.g. a phosphorous oxyhalide such as phosphorous oxychloride to give a 1-halo or 1,5-dihalo-2,6-napthyridine respectively. In the case of 1,5-dihalo-2,6-napthyridines each halogen atom may be substituted separately by a reagent such as $HL^2Ar^2AlkN(R^2)H$ or $HL^3(Alk^2)_rL^4(R^4)_u$ by the particular methods just described above.

2,6- and 2,7-Napthyridine N-oxides and N,N'-dioxides may be generated from the corresponding 2,6- and 2,7-napthyridines by the general methods of synthesis of N-oxides described below or they may be synthesised by the methods of Numata, A. et al (Synthesis, 1999, 306–311).

Further alkylating agents of formula $Ar^1X^1$ in which, for example, $Ar^1$ represents a 2,6-naphthyridine, may be prepared by the methods of Giacomello G. et al (Tetrahedron Letters 1965, 1117–1121), Tan, R. and Taurins, A. (Tetrahedron Letters 1965, 2737–2744), Ames, D. E. and Dodds, W. D. (J. Chem. Soc. Perkin 1 1972, 705–710) and Alhaique, F. et al (Tetdrahedron Letters, 1975, 173–174).

Further alkylating agents of formula $Ar^1X^1$ in which, for example, $Ar^1$ represents a 2,7-naphthyridin-1-yl group, may be prepared by the methods of Wenkert E. et al [J. Am. Chem. Soc. 89, 6741–5, (1967) and Aust. J. Chem. 433, (1972)] and Sheffeld D. J. [J. Chem.Soc. Perkin Trans. 1, 2506 (1972)]. Further alkylating gents of formula $Ar^1X^1$ in which $Ar^1$ represents an isoquinolin-1-yl group may be prepared by the methods of Falk H. et al [Monatsch Chem. 25, 325–33 (1994)] and Deachy, L. W. et al [Aust. J. Chem. 42, 1029–34 (1989)].

In a further example intermediates of formula $R^1R^2NH$ may be obtained by reaction of a compound of formula $Ar^1L^2H$ with a compound of formula $X^1Ar^2AlkN(R^2)H$ under the reaction conditions just described Compounds of formula $Ar^1L^2H$ in which, for example $Ar^1$ represents a 2,6- or 2,7-naphthyridine and $L^2$ is a —$N(R^8)$— group, may be prepared from substituted 4-cyano-3-cyanomethylpyridines by the methods of Alhaique, F . et al [ibid and Gazz. Chim. Ital. 105, 1001–1009 (1975)], from 3-formylpyridines by the methods of Molina, P. at al [Tetrahedron, 48, 4601–4616, (1992)] or by the methods described in U.S. Pat. No. 3,038,367.

Compounds of formula $Ar^1L^2H$ in which $Ar^1$ represents an isoquinidin-1-yl group and $L^2$ is a —$N(R^8)$— group may be prepared by the methods of Bodmer, J. et al [J. Med. Chem. 31, 1036–7 (1988)] and Milino, P. et al [J. Chem. Soc. Perkin Trans. 1, 1727–31, (1990)].

In another example, compounds containing a —$L^1H$ or —$L^2H$ or group as defined above may be functionalised by acylation or thioacylation, for example by reaction with one of the alkylating agents just described but in which $X^1$ is replaced by a —$C(O)X^2$, —$C(S)X^2$, —$N(R^8)COX^2$ or —$N(R^8)C(S)X^2$ group in which $X^2$ is a leaving atom or group as described for $X^1$. The reaction may be performed in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or an amide, e.g. dimethylformamide, at for example ambient temperature. Alternatively, the acylation may be carried out under the same conditions with an acid (for example one of the alkylating agents described above in which $X^1$ is replaced by a —$CO_2H$ group) in the presence of a condensing agent, for example a diimide such as 1-(3-dimethylaminopropyl)-3-ethylcarbodiimide or N,N'-dicyclohexylcarbodiimide, advantageously in the presence of a catalyst such as a N-hydroxy compound e.g. a N-hydroxytriazole such as 1-hydroxybenzotriazole. Alternatively the acid may be reacted with a chloroformate, for example ethylchloroformate, prior to the desired acylation reaction In a further example compounds may be obtained by sulphonylation of a compound containing an —OH group by reaction with one of the above alkylating agents but in which $X^1$ is replaced by a —S(O)Hal or —$SO_2Hal$ group in which Hal is a halogen atom such as chlorine atom] in the presence of a base, for example an inorganic base such as sodium hydride in a solvent such as an amide, e.g. a substituted amide such as dimethylformamide at for example ambient temperature.

In another example, compounds containing a —$L^1H$ or —$L^2H$ group as defined above may be coupled with one of the alkylation agents just described but in which $X^1$ is replaced by an —OH group in a solvent such as tetrahydrofuran in the presence of a phosphine, e.g. triphenylphosphine and an activator such as diethyl, diisopropyl- or dimethylazodicarboxylate.

In a further example, ester groups —$CO_2R^5$, —$CO_2R^{11}$ or —$CO_2Alk^7$ in the compounds may be converted to the corresponding acid [—$CO_2H$] by acid- or base-catalysed hydrolysis depending on the nature of the groups $R^5$, $R^{11}$ or $Alk^7$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an alkali metal hydroxide, e.g. lithium hydroxide in an aqueous alcohol, e.g. aqueous methanol.

In a further example, —$OR^5$ or —$OR^{14}$ groups [where $R^5$ or $R^{14}$ each represents an alkyl group such as methyl group] in compounds of formula (1) may be cleaved to the corresponding alcohol —OH by reaction with boron tribromide in a solvent such as a halogenated hydrocarbon, e.g. dichloromethane at a low temperature, e.g. around $-78°$ C.

Alcohol [—OH] groups may also be obtained by hydrogenation of a corresponding —$OCH_2R^{14}$ group (where $R^{14}$ is an aryl group) using a metal catalyst, for example palladium on a support such as carbon in a solvent such as ethanol in the presence of ammonium formate, cyclohexadiene or hydrogen, from around ambient to the reflux temperature. In another example, —OH groups may be generated from the corresponding ester [$CO_2Alk^7$ or $CO_2R^5$] or aldehyde [—CHO] by reduction, using for example a complex metal hydride such as lithium aluminium hydride or sodium borohydride in a solvent such as methanol.

In another example, alcohol —OH groups in the compounds may be converted to a corresponding —$OR^5$ or —$OR^{14}$ group by coupling with a reagent $R^5OH$ or $R^{14}OH$ in a solvent such as tetrahydrofuran in the presence of a phosphine, e.g. triphenylphosphine and an activator such as diethyl-, diisopropyl-, or dimethylazodicarboxylate.

Aminosulphonylamino [—$NHSO_2NHR^3$ or —$NHSO_2NHAr^1$] groups in the compounds may be obtained, in another example, by reaction of a corresponding amine [—$NH_2$] with a sulphamide $R^3NHSO_2NH_2$ or $Ar^1NHSO_2NH_2$ in the presence of an organic base such as pyridine at an elevated temperature, e.g. the reflux temperature.

In another example compounds containing a —$NHCSAr^1$, —$CSNHAr^1$, —$NHCSR^3$ or —$CSNHR^3$ may be prepared by treating a corresponding compound containing a —$NHCOAr^1$, —$CONHAr^1$, —$NHCOR^3$ or —$CONHR^3$ group with a thiation reagent, such as Lawesson's Reagent, in an anhydrous solvent, for example a cyclic ether such as tetrahydrofuran, at an elevated temperature such as the reflux temperature.

In a further example amine (—$NH_2$) groups may be alkylated using a reductive alkylation process employing an aldehyde and a borohydride, for example sodium triacetoxyborohyride or sodium cyanoborohydride, in a solvent such as a halogenated hydrocarbon, e.g. dichloromethane, a ketone such as acetone, or an alcohol, e.g. ethanol, where necessary in the presence of an acid such as acetic acid at around ambient temperature.

In a further example, amine [—$NH_2$] groups in compounds of formula (1) may be obtained by hydrolysis from a corresponding imide by reaction with hydrazine in a solvent such as an alcohol, e.g. ethanol at ambient temperature.

In another example, a nitro [—$NO_2$] group may be reduced to an amine [—$NH_2$], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid.

Aromatic halogen substituents in the compounds may be subjected to halogen-metal exchange with a base, for example a lithium base such as n-butyl or t-butyl lithium, optionally at a low temperature, e.g. around $-78°$ C., in a solvent such as tetrahydrofuran and then quenched with an electrophile to introduce a desired substituent. Thus, for example, a formyl group may be introduced by using dimethylformamide as the electrophile; a thiomethyl group may be introduced by using dimethyldisulphide as the electrophile.

In another example, sulphur atoms in the compounds, for example when present in a linker group $L^1$ or $L^2$ may be oxidised to the corresponding sulphoxide or sulphone using an oxidising agent such as a peroxy acid, e.g. 3-chloroperoxybenzoic acid, in an inert solvent such as a halogenated hydrocarbon, e.g. dichloromethane, at around ambient temperature.

In another example compounds of formula $Ar^1X^1$ (where $X^1$ is a halogen atom such as a chlorine, bromine or iodine atom) may be converted to further intermediate compounds such as $Ar^1CO_2R^{20}$ (in which $R^{20}$ is an optionally substituted alkyl, aryl or heteroaryl group), $Ar^1CHO$, $Ar^1CHCHR^{20}$, $Ar^1CCR^{20}$, $Ar^1N(R^{20})H$, $Ar^1N(R^{20})_2$ under such well know and commonly used palladium mediated reaction conditions as are to be found in the general reference texts Encyclopedia of Reagents for Organic Synthesis, Editor-in Chief Paquette, L. A., John Wiley and Sons, 1995 and Comprehensive Organic Functional Group Transformations, Editors-in-Chief Katritzky, A. R. et al, Pergamon, 1995.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate base in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above.

Chromatography, recrystallisation and other conventional separation procedures may also be used with intermediates or final products where it is desired to obtain a particular geometric isomer of the invention.

The following Examples illustrate the invention. All temperatures are in °C. The following abbreviations are used:

NMM—N-methylmorpholine;
MeOH—methanol;
DCM—dichloromethane;
DIPEA—diisopropylethylamine;
Pyr—pyridine;
DMSO—dimethylsulphoxide;
$Et_2O$—diethylether;
THF—tetrahydrofuran,
FMOC—9-fluorenylmethoxycarbonyl;
DBU—1,8-diazabicyclo[5.4.0]undec-7-ene EtOAc—ethyl acetate
BOC—butoxycarbonyl;
AcOH—acetic acid;
EtOH—ethanol;
Ar—aryl;
iPr—isopropyl;
Me—methyl;
DMF—N,N-dimethylformamide;
All NMR's were obtained at 300 MHz or 400 MHz.

Intermediate 1

2-Propylhexahydro-1-H-indend-1,3(2H)-dione

To $AlCl_3$ (6.07 g, 45.5 mmol) in nitromethane (15 ml) was added a nitromethane (5 ml) solution of valeric anhydride (3.53 g, 19.0 mmol) and cis-1,2-cyclohexane dicarboxylic anhydride (2.93 g, 19.0 mmol). The reaction was heated at 100° overnight, poured into water (100 ml) was extracted into EtOAc. The EtOAc was extracted with 1M NaOH; this aqueous layer acidified with 1M HCl, the product extracted back into EtOAc, dried ($MgSO_4$) and the solvent removed. The residue was taken up in DCM and insoluble 1,2-cyclohexane dicarboxylic acid removed by filtration. The solvent was removed from the filtrate and the residue purified by column chromatogrpahy (silica; DCM then 30% EtOAc in hexane) to give the title compound (3.97 mg, 11%) as a waxy beige solid. $\delta H$ ($CD_3OD$) 2.68 (2H,m ), 2.10 (2H, t, J 7.4 Hz), 1.83 (2H, br). 1.63 (2H, br), 1.44 (6H, m), 0.89 (3H, t, J 7.4 Hz), m/z ($ES^+$, 70V) 195 ($MH^+$).

EXAMPLE 1

(2S-Ethyl-3-[4-(2,6-naphthyridin-1-ylamino) phenyl]-2-[(1-oxo-3a,4,7,7a-tetrahydro-1-H-inden-3-yl)amino]propionate A solution of (S)-ethyl-3-[4-(2,6-naphthyrid-1-ylamino) phenyl]-2-amino propionate (prepared from 1-chloro-2,6-naphthyridine and N-BOC-L-4-aminophenylalanine ethyl ester) (597 mg, 1.78 mmol) and 3a,4,7,7a-tetrahydro-1,3-indandione (20 mg, 1.87 mmol) in 1,2-dichloroethane (10 ml) was treated with 4 Å molecular sieves (~1 g) and heated at 80° for 4 days. The solution was filtered concentrated in vacuo and the residue purified by chromatography ($SiO_2$; 98:2–97:3 DCM/MeOH) to give the title compound as an orange solid (251 mg, 30%). $\delta H$ ($CD_3OD$) 9.13 (1H, s), 8.58 (1H, d, J 6.0hH), 8.23 (1H, d, J 5.1 Hz), 8.09 (1H, d, J 5.8 Hz), 7.69 (1H, d J 8.3 Hz), 7.67 (1H, d, J 8.3 Hz), 7.24 (3H, m), 5.90–5.60 (2H, m), 4.97–4.95 (1H, 2×d), 4.30 (2H, m), 4.18 (2H,q, J 7.1 Hz), 3.21 (1H, m), 3.15–3.00 (2H, m), 2.61 (1H, m), 2.45–2.00 (4H, m), 1.27, 1.24 (3H, 2×t, J 7.1 Hz). m/z ($ES^+$, 70V) 469 ($MH^+$).

EXAMPLE 2 and EXAMPLE 3

(2S)-3-[4-(2,6-Naphthyridin-1-ylamino)phenyl]-2-[(1-oxo-3a,4,7,7a-tetrahydro-1H-inden-3-yl)amino] propionic acid A solution of Example 1 (251 mg, 0.54 mmol) in THF (2 ml) and water (2 ml) was treated with $LiOH.H_2O$ (34 mg, 0.804 mmol) and stirred for 30 min. The mixture was concentrated in vacuo and purified by chromatography ($SiO_2$; DCM:MeOH:AcOH:$H_2O$, 200:20:3:2) to give the two isomers of the title compound Example 2 (103 mg, 44%) and Example 3 (104 mg, 44%) as yellow solids.

EXAMPLE 2

$\delta H$ ($d^6$-DMSO) 9.31 (1H, s), 9.23 (1H, s), 8.68 (1H, d, J 5.9 Hz), 8.40 (1H, d, J 5.9 Hz), 8.15 (1H, d, J 5.7 Hz), 7.78

(2H, m), 7.54 (1H, d, J 8.0 Hz), 7.28 (1H, d, J 5.8 Hz), 7.23 (2H, d, J 8.5 Hz), 5.76 (2H, m), 4.76 (1H, s), 4.06 (1H, m), 3.10 (1H, dd, J 13.8, 5.5 Hz), 3.01, 2.91 (2H, m), 2.41 (1H, m), 2.28 (1H, m), 2.17 (2H, m) 2.02 (1H, m). m/z (ES$^+$, 70V), 441 (MH$^+$).

EXAMPLE 3

δH (d$^6$-DMSO) 9.30 (1H, s), 9.23 (1H, s), 8.68 (1H, d, J 5,9 Hz), 8.40 (1H, d, J 5.9 Hz), 8.14 (1H, d, J 5.7 HZ), 7.79 (2H, m), 7.62 (1H, d), 7.28 (1H, d, J 5.8 Hz), 7.23 (2H, d, J 1.4 Hz), 5.68 (1H, m), 5.59 (1H, m), 4.74 (1H, s), 4.01 (1H, m), 3.11 (1H, dd, J 14.1, 4.9 Hz), 3.03–2.93 (2H, m), 2.41 (1H, m), 2.20–1.92 (4H, m). m/z (ES$^+$, 70V) 441 (MH$^+$).

EXAMPLE 4

(2S)-Ethyl-3-[4-(2,7-naphthyridin-1-ylamino) phenyl]-2-[(1-oxo-2-propyl-3a,4,5,6,7,7a-hexahydro-1-H-inden-3-yl)amino]propionate To Intermediate 1 (207 mg, 1.1 mmol) in nitromethane (5 ml) was added ethyl-(S)-3-[4-(2,7-naphthyrid-1-ylamino) phenyl]-2-amino propionate (prepared from 1-chloro-2,7-naphthyridine and N-BOC-L-4-aminophenylalanine ethyl ester) (359 mg, 1.1 mmol) followed by acetic acid (2 drops) and Na$_2$SO$_4$ (0.5 g). The reaction was heated at 120° for 3 days, the solvent removed and the residue purified by chromatography (silica; 75–85% EtOAc in hexane) to yield the title compound (213 mg, 39%) as a yellow/orange solid as a 1:1 mixture of diastereoisomers. δH (CD$_3$OD) 9.65, 9.63 (1H, 2×s), 8.57 (1H, d, J 5.7 Hz), 8.11 (1H, d, J 5.8 Hz), 7.65 (3H, m), 7.29, 7.24 (2H, 2×d, J 8.5 and 8.5 Hz), 7.07 (1H, d, J 5.8 Hz), 4.54, 4.48 (1H, 2×m), 4.26, 4.21 (2H, 2×q, J 7.2 Hz),.3.15–3.00 (2H, m), 2.92, 2.47 (1H, 2×br), 2.13 (2H, m), 1.96 (2H, br), 1.62–1.20 (1H, br m), 0.89, 0.88 (3H, 2×t, J 7.4, 7.4 Hz). m/z (ES$^+$, 70V), 513 (MH$^+$).

EXAMPLE 5

2S-3-[4-(2,7-Naphthyridin-1-ylamino)phenyl]-2-[(1-oxo-2-propyl)-3a,4,5,6,7,7a-hexahydro-1-H-inden-3-yl)amino]propionic acid To the compound of Example 5 (149 mg, 0.29 mmol) in THF (2 ml) was added LiOH.H$_2$O (28 mg, 0.44 mmol) followed by H$_2$O (1 ml). After 30 min the solvent was removed and the residue purified by chromatography 300:20:3:2 DCM. MeOH:AcOH:H$_2$O) to give the title compound (122 mg, 87%) as a yellow solid and as a 1:1 mix of diastereoisomers. δH (DMSO) 9.83, 9.81 (1H, 2×s), 9.51, 9.50 (1H, 2×s), 8.65 (1H, d, J 5.6 Hz), 8.14, 8.13 (1H, 2×t, J 5.7 Hz), 7.72, 7.70 (2H, m), 7.68 (1H, d, J 5.6 Hz), 7.27, 7.22 (2H, 2×d, J 8.4 Hz), 7.11 (1H, d, J 5.8 Hz), 6.87 (1H, br d, J 9.8 Hz), 4.28, 4.18 (1H, 2×br), 3.18–2.92 (2H, m), 2.67 (1H, m), 2.21 (1H, m), 2.03 (2H, m), 1.97–1.82 (2H, br), 1.30–0.78 (8H, br), 0.80 (3H, m). m/z (ES$^+$, 70V) 485 (MH$^+$).

The following assays can be used to demonstrate the potency and selectivity of the compounds according to the invention. In each of these assays an IC$_{50}$ value was determined for each test compound and represents the concentration of compound necessary to achieve 50% inhibition of cell adhesion where 100%=adhesion assessed in the absence of the test compound and 0%=absorbance in wells that did not receive cells.

$\alpha_4\beta_1$ Integrin-dependent Jurkat Cell Adhesion to VCAM-Ig 96 well NUNC plates were coated with F(ab)$_2$ fragment goat anti-human IgG Fcγ-specific antibody [Jackson Immuno Research 109-006-098: 100 μl at 2 μg/ml in 0.1 M NaHCO$_3$, pH 8.4], overnight at 4°. The plates were washed (3×) in phosphate-buffered saline (PBS) and then blocked for 1 h in PBS/1% BSA at room temperature on a rocking platform. After washing (3× in PBS) 9 ng/ml of purified 2d VCAM-Ig diluted in PBS/1% BSA was added and the plates left for 60 minutes at room temperature on a rocking platform. The plates were washed (3× in PBS) and the assay then performed at 37° for 30 min in a total volume of 200 μl containing 2.5×10$^5$ Jurkat cells in the presence or absence of titrated test compounds.

Each plate was washed (2×) with medium and the adherent cells were fixed with 100 μl methanol for 10 minutes followed by another wash. 100 μl 0.25% Rose Bengal (Sigma R4507) in PBS was added for 5 minutes at room temperature and the plates washed (3×) in PBS. 100 μl 50% (v/v) ethanol in PBS was added and the plates left for 60 min after which the absorbance (570 nm) was measured.

$\alpha_4\beta_7$ Integrin-dependent JY Cell Adhesion to MAdCAM-Ig

This assay was performed in the same manner as the $\alpha_4\beta_1$ assay except that MAdCAM-Ig (150 ng/ml) was used in place of 2d VCAM-Ig and a sub-line of the β-lympho blastoid cell-line JY was used in place of Jurkat cells. The IC$_{50}$ value for each test compound was determined as described in the $\alpha_4\beta_1$ integrin assay.

$\alpha_5\beta_1$ Integrin-dependent K562 Cell Adhesion to Fibronectin 96 well tissue culture plates were coated with human plasma fibronectin (Sigma F0895) at 5 μg/ml in phosphate-buffered saline (PBS) for 2 hr at 37° C. The plates were washed (3× in PBS) and then blocked for 1 h in 100 μl PBS/1% BSA at room temperature on a rocking platform. The blocked plates were washed (3× in PBS) and the assay then performed at 37° C in a total volume of 200 μl containing 2.5×10$^5$ K562 cells, phorbol-12-myristate-13-acetate at 10 ng/ml, and in the presence or absence of titrated test compounds. Incubation time was 30 minutes. Each plate was fixed and stained as described in the $\alpha_4\beta_1$ assay above.

$\alpha_m\beta_2$-dependent Human Polymorphonuclear Neutrophils Adhesion to Plastic 96 well tissue culture plates were coated with RPMI 1640/10% FCS for 2 h at 37° C. 2×10$^5$ freshly isolated human venous polymorphonuclear neutrophils (PMN) were added to the wells in a total volume of 200 μl in the presence of 10 ng/ml phorbol-12-myristate-13-acetate, and in the presence or absence of test compounds, and incubated for 20 min at 37° C. followed by 30 min at room temperature. The plates were washed in medium and 100 μl 0.1% (w/v) HMB (hexadecyl trimethyl ammonium bromide, Sigma H5882) in 0.05M potassium phosphate buffer, pH 6.0 added to each well. The plates were then left on a rocker at room temperature for 60 min. Endogenous peroxidase activity was then assessed using tetramethyl benzidine (TMB) as follows: PMN lysate samples mixed with 0.22% H$_2$O$_2$ (Sigma) and 50 μg/ml TMB (Boehringer Mannheim) in 0.1M sodium acetate/citrate buffer, pH 6.0 and absorbance measured at 630 nm.

αIIb/β$_3$-dependent Human Platelet Aggregation

Human platelet aggregation was assessed using impedance aggregation on the Chronolog Whole Blood Lumiaggregometer. Human platelet-rich plasma (PRP) was obtained by spinning fresh human venous blood anticoagulated with 0.38% (v/v) tri-sodium citrate at 220×g for 10 min and diluted to a cell density of 6×10$^8$/ml in autologous plasma. Cuvettes contained equal volumes of PRP and filtered Tyrode's buffer (g/liter:NaCl 8.0; MgCl$_2$.H$_2$O 0.427; CaCl$_2$ 0.2; KCl 0.2; D-glucose 1.0; NaHCO$_3$ 1.0; NaHPO$_4$.2H$_2$O 0.065). Aggregation was monitored following addition of 2.5 μM ADP (Sigma) in the presence or absence of inhibitors.

In the above assays the preferred compounds of the invention in which $R^1$ is an $\alpha_4$ integrin binding group, such as the compounds of the Examples generally have $IC_{50}$ values in the $\alpha_4\beta_1$ and $\alpha_4\beta_7$ assays of 1 μM and below. In the other assays featuring α integrins of other subgroups the same compounds had $IC_{50}$ values of 50 μM and above thus demonstrating the potency and selectivity of their action against $\alpha_4$ integrins.

What is claimed is:

1. A compound of formula (1):

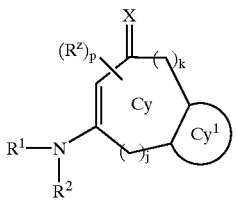

(1)

wherein $R^1$ is a group $Ar^1L^2Ar^2Alk$- in which $Ar^1$ is an optionally substituted aromatic or heteroaromatic group, $L^2$ is a covalent bond or a linker atom or group, $Ar^2$ is an optionally substituted arylene or heteroarylene group and Alk is a chain —$CH_2$—$CH(R)$—, —$CH=C(R)$— or

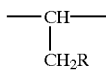

in which R is a carboxylic acid (—$CO_2H$) or a derivative or biostere thereof;

$R^2$ is a hydrogen atom or a $C_{1-6}$alkyl group;

X is an O or S atom or the group $NR^{30}$ in which $R^{30}$ is an optionally substituted aliphatic, heteroaliphatic, cycloaliphatic, heterocycloaliphatic, aromatic or heteroaromatic group;

j and k is each zero or the integer 1 or 2 provided that the sum of j and k is zero or the integer 1 or 2;

$Cy^1$ is an optionally substituted cycloaliphatic, heterocycloaliphatic, aromatic or heteroaromatic group which incorporates two adjacent carbon atoms of the ring Cy within its ring structure such that the bond between these two atoms may be saturated or unsaturated;

$R^z$ which may be present on any available carbon atom of the ring Cy is selected from a halogen atom or -$(Alk^4)_v$ $L^1(Alk^1)_n(R^3)_s$ atom or group in which $Alk^4$ is a straight or branched $C_{1-3}$alkylene chain, v is zero or the integer 1, $L^1$ is a covalent bond or a linker atom or group, n is zero or the integer 1, $Alk^1$ is an optionally substituted aliphatic chain, s is the integer 1, 2 or 3 and $R^3$ is a hydrogen atom or a —CN, —$NO_2$ or optionally substituted heteroaliphatic, cycloaliphatic, heterocycloaliphatic, polycyclo-aliphatic, heteropolycycloaliphatic, aromatic or heteroaromatic group provided that when v and n are zero and $L^1$ is a covalent bond and s is the integer 1;

p is zero or the integer 1, 2 or 3;

and the salts, solvates, hydrates and N-oxides thereof.

2. A compound according to claim 1 in which Alk is a chain —$CH_2$—$CH(R)$— or

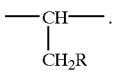

3. A compound according to claim 1 in which R is a carboxylic acid (—$CO_2H$) group.

4. A compound according to claim 1 in which R is an esterified carboxyl group of formula —$CO_2Alk^7$;

wherein $AlK^7$ is optionally substituted and is $C_{1-8}$alkyl, $C_{2-8}$alkenyl, $C_{2-8}$alkynyl, $C_{3-8}$cycloalkyl, $C_{3-8}$cycloalkyl$C_{1-8}$alkyl, $C_{3-8}$heterocycloalkyl$C_{1-6}$alkyl, $C_{1-6}$alkyloxy$C_{1-6}$alkyl, $C_{1-6}$alkylthio$C_{1-6}$alkyl, $C_{1-6}$alkylsulfinyl$C_{1-6}$alkyl, $C_{1-6}$alkylsulfonyl$C_{1-6}$alkyl, $C_{3-8}$cycloalkyloxy$C_{1-6}$alkyl, $C_{3-8}$cycloalkylthio$C_{1-6}$alkyl, $C_{3-8}$cycloalkylsulfinyl$C_{1-6}$alkyl, $C_{3-8}$cycloalkylsulfonyl$C_{1-6}$alkyl, $C_{1-6}$alkyloxycarbonyl$C_{1-6}$alkyl, $C_{1-6}$alkyloxycarbonyl$C_{1-6}$alkenyl, $C_{1-6}$alkyloxycarbonyloxy$C_{1-6}$alkyl, $C_{1-6}$alkyloxycarbonyloxy$C_{1-6}$alkenyl, $C_{3-8}$cycloalkyloxycarbonyloxy$C_{1-6}$alkyl, N-di-$C_{1-8}$alkylamino$C_{1-8}$alkyl, N-$C_{6-12}$aryl-N-$C_{1-6}$alkylamino$C_{1-6}$alkyl, N-di-$C_{1-8}$alkylcarbamoyl$C_{1-8}$alkyl, $C_{6-10}$aryl$C_{1-6}$alkyl, $C_{6-10}$aryl, $C_{6-10}$aryloxy$C_{1-8}$alkyl, $C_{6-12}$arylthio$C_{1-8}$alkyl, $C_{6-12}$arylsulfinyl$C_{1-8}$alkyl, $C_{6-12}$arylsulfonyl$C_{1-8}$alkyl, $C_{1-8}$alkanoyloxy$C_{1-8}$alkyl, $C_{4-8}$imido$C_{1-8}$alkyl, or $C_{6-12}$aroyloxy$C_{1-8}$alkyl; each of which is optionally substituted;

or $AlK^7$ is a triglyceride group.

5. A compound according to claim 1 in which $R^2$ is a hydrogen atom.

6. A compound according to claim 1 in which $Ar^2$ is an optionally substituted phenylene group.

7. A compound according to claim 1 in which $Ar^1$ is an optionally substituted phenyl or five-, six- or ten-membered heteroaromatic group.

8. A compound according to claim 7 in which $Ar^1$ is an optionally substituted pyridyl, pyrimidinyl, naphthyridinyl, quinolinyl or isoquinolinyl group.

9. A compound according to claim 1 in which j and k is each zero, p is zero or the integer 1 and Cy—$Cy^1$ has the formula (2e):

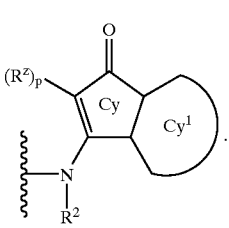

(2e)

10. A compound according to claim 1 in which j is the integer 1 and h is zero or h is the integer 1 and j is zero, p is zero or the integer 1 or 2 and Cy—$Cy^1$ has the formula (2f) or (2g):

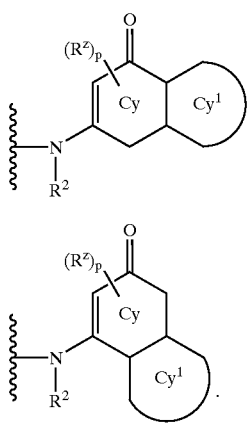

(2f)

(2g)

11. A compound according to claim 1 in which $Cy^1$ is an optionally substituted cycloaliphatic or heterocycloaliphatic group.

12. A compound according to claim 1 in which v in the group $R^z$ is zero, $Alk^1$ is an aliphatic chain, s is the integer 1 and $R^3$ is a hydrogen atom.

13. A compound according to claim 12 in which -$Alk^1R^3$ is an optionally substituted $C_{1-6}$alkyl, alyl (—$CH_2CHCH_2$) or propargyl (—$CH_2CCH$) group.

14. A compound according to claim 1 in which $L^1$ is a covalent bond.

15. A compound according to claim 1 in which $L^1$ is a —$N(R^8)$— group; wherein $R^8$ is a hydrogen atom or an optionally substituted straight or branched $C_{1-6}$alkyl group.

16. A compound which is selected from the group consisting of:

(2S)-3-[4-(2,6-Naphthyridin-1-ylamino)phenyl]-2-[(1-oxo-3a,4,7,7a-tetrahydro-1H-inden-3-yl)amino]propionic acid;

(2S)-3-[4-(2,7-Naphthyridin-1-ylamino)phenyl]-2-[(1-oxo-2-propyl-3a,4,5,6,7a-hexahydro-1H-inden-3-yl)amino]propionic acid;

and the salts, solvates, hydrates, N-oxides and carboxylic acid esters thereof.

17. A pharmaceutical composition comprising a compound according to claim 1 together with one or more pharmaceutically acceptable carriers, excipients or diluents.

18. A method for the prophylaxis or treatment of a disease or disorder in a mammal in which the extravasation of leukocytes plays a role, comprising administering to a mammal in need of such treatment a therapeutically effective amount of a compound according to claim 1.

19. A method according to claim 18 wherein said disease or disorder is selected from the group consisting of inflammatory arthritis, multiple sclerosis, allograft, rejection, diabetes, inflammatory dermatoses, asthma and inflammatory bowel disease.

20. A method according to claim 19 wherein said inflammatory arthritis is selected from the group consisting of rheumatoid arthritis, vasculitis and polydermatomyositis.

21. A method according to claim 19 wherein said inflammatory arthritis is selected from the group consisting of prosiasis and dermatitis.

22. A method of inhibiting, in a mammal, the binding of α4 integrins to the ligands thereof, comprising administering to the mammal an effecting amount of a compound according to claim 1.

23. A method according to claim 21 wherein the α4 integrins are selected from the group consisting of α4β1 and α4β7 integrins.

* * * * *